United States Patent
Snyder et al.

(10) Patent No.: US 12,396,992 B2
(45) Date of Patent: Aug. 26, 2025

(54) ORGANIC COMPOUNDS

(71) Applicant: INTRA-CELLULAR THERAPIES, INC., New York, NY (US)

(72) Inventors: Gretchen Snyder, New York, NY (US); Lawrence P. Wennogle, Hillsborough, NJ (US); Jennifer O'Brien, New York, NY (US); Joseph Hendrick, New York, NY (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 1058 days.

(21) Appl. No.: 17/421,303

(22) PCT Filed: Jan. 7, 2020

(86) PCT No.: PCT/US2020/012578
§ 371 (c)(1),
(2) Date: Jul. 7, 2021

(87) PCT Pub. No.: WO2020/146384
PCT Pub. Date: Jul. 16, 2020

(65) Prior Publication Data
US 2022/0072003 A1 Mar. 10, 2022

Related U.S. Application Data

(60) Provisional application No. 62/789,499, filed on Jan. 7, 2019.

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC ........ A61K 31/519; A61P 35/00; A61P 25/08; C07D 401/14; C07D 403/04; C07F 7/08
See application file for complete search history.

(56) References Cited

U.S. PATENT DOCUMENTS

| | | |
|---|---|---|
| 4,690,935 A | 9/1987 | Taylor et al. |
| 8,273,751 B2 | 9/2012 | Li |
| 8,633,180 B2 | 1/2014 | Li et al. |
| 8,664,207 B2 | 3/2014 | Li et al. |
| 9,073,936 B2 | 7/2015 | Li et al. |
| 9,545,406 B2 | 1/2017 | Wennogle |
| 9,708,294 B2 | 7/2017 | Li et al. |
| 9,884,872 B2 | 2/2018 | Li et al. |
| 10,092,575 B2 | 10/2018 | Branstetter et al. |
| 10,150,774 B2 | 12/2018 | Li et al. |
| 10,682,355 B2 | 6/2020 | Wennogle |
| 10,849,862 B2 | 12/2020 | Kawakami et al. |
| 11,291,666 B2 | 4/2022 | Snyder et al. |
| 11,504,372 B2 | 11/2022 | Wennogle |
| 2014/0128353 A1 | 5/2014 | Bannister et al. |
| 2014/0235556 A1 | 8/2014 | Halse et al. |
| 2015/0017267 A1 | 1/2015 | Guedes et al. |
| 2016/0324860 A1 | 11/2016 | Hendrick et al. |
| 2016/0362489 A1 | 12/2016 | Yang |
| 2020/0085782 A1 | 3/2020 | Gallatin et al. |
| 2021/0205310 A1 | 7/2021 | Wennogle et al. |
| 2021/0338679 A1 | 11/2021 | Li et al. |
| 2022/0354851 A1 | 11/2022 | Li et al. |

FOREIGN PATENT DOCUMENTS

| | | | |
|---|---|---|---|
| WO | WO 2006/133261 A2 | 12/2006 | |
| WO | WO 2006/133261 A3 | 12/2006 | |
| WO | WO 2016/022893 A1 | 2/2016 | |
| WO | 2017/011831 A1 | 1/2017 | |
| WO | WO 2018/093591 A1 | 5/2018 | |
| WO | WO 2019/046778 A1 | 3/2019 | |
| WO | 2019/227004 A1 | 11/2019 | |
| WO | WO 2020/146384 * | 1/2020 | ........... A61K 31/519 |
| WO | 2023/173131 A2 | 9/2023 | |

OTHER PUBLICATIONS

Levy et al., "Phosphodiesterase Function and Endocrine Cells: Links to Human Disease and Roles in Tumor Development and Treatment," *Current Opinion in Pharmacology*, vol. 11, p. 689-697, (2011).

Snyder et al., "Suppression of CNS Inflammation by Phosphodiesterase-1 (PDE1) Inhibitors: Toward New Treatments for Neurodegenerative Diseases," Database Embase, Database Accession No. EMB-620612543, Alzheimer's Association International Conference AAIC 2017 in London, 2 pages, Abstract Only.

Abusnina et al., "Anti-Proliferative Effect of Curcumin on Melanoma Cells is Mediated by PDE1A Inhibition that Regulates the Epigenetic Integrator UHRF1," *Mol. Nutr. Food Res.*, vol. 55, pp. 1677-1689, (2011).

Ahlström et al., "Cyclic Nucleotide Phosphodiesterases (PDEs) in Human Osteoblastic Cells; The Effect of PDE Inhibition on cAMP Accumulation," *Cell Mol Biol Lett*, vol. 10, No. 10, pp. 305-319, (2005).

Ahmad et al., "Cyclic Nucleotide Phosphodiesterases: Important Signaling Modulators and Therapeutic Targets," *Oral Diseases*, vol. 21, pp. e25-e50, (2015).

Almahariq et al., "Pharmacological Inhibition and Genetic Knockdown of Exchange Protein Directly Activated by cAMP 1 Reduce Pancreatic Cancer Metastasis In Vivo," *Molecular Pharmacology*, vol. 87, No. 2, pp. 142-149, (2015).

(Continued)

*Primary Examiner* — Erich A Leeser
(74) *Attorney, Agent, or Firm* — Hoxie & Associates LLC

(57) ABSTRACT

The disclosure relates to the use of phosphodiesterase 1 (PDE1) inhibitors for the treatment of cancers and tumors, including for inhibiting tumor recruitment of macrophages and other cells to the tumor or cancer, for complementing and enhancing checkpoint inhibitor therapies, and for mitigating the side effects (i.e., inflammatory-related adverse events) associated with checkpoint inhibitor therapies.

22 Claims, 13 Drawing Sheets

(56) References Cited

OTHER PUBLICATIONS

Argyle et al., "Targeting Macrophage-Recruiting Chemokines as a Novel Therapeutic Strategy to Prevent the Progression of Solid Tumors," *Frontiers in Immunology*, vol. 9, No. 2629, 15 pages, (2018).

Boyd et al., "cAMP-Phosphodiesterase PDE4D as a Target for Colon Cancer Therapy," *The FASEB Journal*, vol. 31, No. 1, 2 pages (2017).

Brodbelt et al., "Glioblastoma in England: 2007-2011," *Eur J Cancer*, vol. 51, pp. 533-542, (2015).

Chen et al., "cAMP Inhibits Cell Migration by Interfering with Rac-induced Lamellipodium Formation," *Journal of Biological Chemistry*, vol. 283, No. 20, pp. 13799-13805, (2008).

Coussens et al., "Inflammation and Cancer," *Nature*, vol. 420, No. 6917, pp. 860-867, (2002).

Daniel et al., "Sensitivity of GBM Cells to cAMP Agonist-mediated Apoptosis Correlates with CD44 Expression and Agonist Resistance with MAPK Signaling," *Cell Death and Disease*, vol. 7, No. e2494, 11 pages, (2016).

Insel et al., "Cyclic AMP is Both a Pro-apoptotic and Anti-apoptotic Second Messenger," *Acta Physiol (Oxf)*, vol. 204, No. 2, pp. 277-287, (2012).

Jang et al., "Adaptation of cAMP Signaling System in SH-SY5Y Neuroblastoma Cells Following Expression of a Constitutively Active Stimulatory G Protein Alpha, Q227L Gsα," *Exp Mol Med*, vol. 33, No. 1, pp. 37-45, (2001).

Jiang et al., "Expression and Regulation of mRNA for Distinct Isoforms of cAMP-Specific PDE-4 in Mitogen-Stimulated and Leukemic Human Lymphocytes," *Cell Biochem Biophys*, vol. 28, pp. 135-160, (1998).

Kim et al., "Antiinflammatory cAMP Signaling and Cell Migration Genes Co-opted by the Anthrax Bacillus," *PNAS*, vol. 105, No. 16, pp. 6150-6155, (2008).

Marko et al., "Cyclic 3',5'-nucleotide Phosphodiesterases: Potential Targets for Anticancer Therapy," *Chem Res Toxicol*, vol. 13, pp. 944-948, (2000).

Medina, A, "Therapeutic Utility of Phosphodiesterase Type I Inhibitors in Neurological Conditions," *Frontiers in Neuroscience*, vol. 5, No. 21, pp. 1-5, (2011).

Pantziarka et al., "Repurposing Drugs in Oncology (ReDO)—Selective PDE5 Inhibitors as Anti-Cancer Agents," *ecancer*, vol. 12, No. 824, 22 pages, (2018).

Peng et al., "Inhibitors of Phosphodiesterase as Cancer Therapeutics," *European Journal of Medicinal Chemistry*, vol. 150, pp. 742-756, (2018).

Rowther et al., "Cyclic Nucleotide Phosphodiesterase-1C (PDE1C) Drives Cell Proliferation Migration and Invasion in Glioblastoma Multiforme Cells In Vitro," *Molecular Carcinogenesis*, vol. 55, pp. 268-279, (2016).

Rybalkin et al., "Calmodulin-stimulated Cyclic Nucleotide Phosphodiesterase (PDE1C) is Induced in Human Arterial Smooth Muscle Cells of the Synthetic, Proliferative Phenotype," *J Clin Invest*, vol. 100, No. 10, pp. 2611-2621, (1997).

Savai et al., "Targeting Cancer with Phosphodiesterase Inhibitors," *Expert Opin. Investig. Drugs*, vol. 19, No. 1, pp. 117-131, (2010).

Shimizu et al., "Characterization of Phosphodiesterase 1 in Human Malignant Melanoma Cell Lines," *AntiCancer Research*, vol. 29, pp. 1119-1122, (2009).

Shiri et al., "Dendrosomal Curcumin Suppresses Metastatic Breast Cancer in Mice by Changing M1/M2 Macrophage Balance in the Tumor Microenvironment," *Asian Pacific Journal of Cancer Prevention*, vol. 16, 7 pages, (2015).

Soon, L., "A Discourse on Cancer Cell Chemotaxis: Where to From Here?", *IUBMB Life*, vol. 59, No. 2, pp. 60-67, (2007).

Stupp et al., "Radiotherapy Plus Concomitant and Adjuvant Temozolomide for Glioblastoma", *N Engl J Med*, vol. 352, No. 10, pp. 987-996, (2005).

Touat et al., "Glioblastoma Targeted Therapy: Updated Approaches from Recent Biological Insights," *Ann. Oncol.*, vol. 28, No. 7, pp. 1457-1472, (2017).

Vitale et al., "A New Therapeutic Strategy Against Cancer: cAMP Elevating Drugs and Leptin," *Cancer Biology & Therapy*, vol. 8, No. 12, pp. 1191-1193, (2009).

Watanabe et al., "Phosphodiesterase 4 Regulates the Migration of B16-F10 Melanoma Cells," *Exp Ther Med*, vol. 4, pp. 205-210, (2012).

"Gene expression," Wikipedia, 17 pages, (2017); accessed on Jul. 18, 2019 at https://en.wikipedia.org/w/index.php?title=Gene_expression&oldid=803718522.

Zong et al., "The Cellular Origin for Malignant Glioma and Prospects for Clinical Advancements," *Expert Rev Mol Diagn.*, vol. 12, No. 4, pp. 383-394, (2012).

Bastin, R. et al., "Salt Selection and Optimized Procedures for Pharmaceutical New Chemical Entities," Organic Process and Research Development, vol. 4, No. 5, pp. 427-435, (2000).

Hayakawa, T. et al., "Enhanced anti-tumor effects of the PD-1/PD-L1 blockade by combining a highly absorptive form of NF-κB/STAT3 inhibitor curcumin," Journal for ImmunoTherapy of Cancer, vol. 2, Suppl. 3, p. P210, (2014).

Johnson, J. et al., "Curcumin for chemoprevention of colon cancer," Cancer Letters, vol. 255, pp. 170-181, (2007).

Li, P. et al., "Discovery of Potent and Selective Inhibitors of Phosphodiesterase 1 for the Treatment of Cognitive Impairment Associated with Neurodegenerative and Neuropsychiatric Diseases," Journal of Medicinal Chemistry, vol. 59, No. 3, pp. 1149-1164, (2016).

Martinez, F. et al., "Genetic Programs Expressed in Resting and IL-4 Alternatively Activated Mouse and Human Macrophages: Similarities and Differences," Blood, vol. 121, No. 9, 13 pages, (2013).

Mietto, B. et al., "Role of IL-10 in Resolution of Inflammation and Functional Recovery after Peripheral Nerve Injury," The Journal of Neuroscience, vol. 35, No. 50, pp. 16431-16442, (2015).

Szajewska, H., "Evidence-based Medicine and Clinical Research: Both are Needed, Neither is Perfect," Annals of Nutrition and Metabolism, vol. 72, No. 3, pp. 13-23, (2018).

Wesserling, M. et al., "Will In Vitro Tests Replace Animal Models in Experimental Oncology?," Journal of Tissue Science and Engineering, vol. 2, No. 1, p. 102e, (2011), Abstract only.

Yue, G. et al., "Combined therapy using bevacizumab and turmeric ethanolic extract (with absorbable curcumin) exhibited beneficial efficacy in colon cancer mice," Pharmacological Research, vol. 111, pp. 43-57, (2016).

Zhao. A. et al., "Recent Advances in the Study of Ca2+/CaM-activated Phosphodiesterases: Expression and Physiological Functions," Adv Second Messenger Phosphoprotein Res, vol. 31, pp. 237-251, (1997).

\* cited by examiner

ORGANIC COMPOUNDS

CROSS-REFERENCE TO RELATED APPLICATIONS

This application is a U.S. National Stage Application under 35 U.S.C. § 371 of International Application No. PCT/US2020/012578, which was filed on Jan. 7, 2020, which claims priority to and the benefit of U.S. Provisional Application Ser. No. 62/789,499, which was filed on Jan. 7, 2019, the contents of each of which are hereby incorporated by reference in their entireties.

FIELD OF DISCLOSURE

The field relates to the use of phosphodiesterase 1 (PDE1) inhibitors for the treatment of cancers and tumors, including for inhibiting recruitment of macrophages and other cells to the tumor or cancer, for inhibiting tumor cell migration and preventing tumor metastasis, for complementing and enhancing checkpoint inhibitor, genome editing and chimeric antigen receptor T-cell (CAR-T) therapies, for preventing and reversing immune suppressive tumor microenvironments, and for mitigating the side effects (i.e., inflammatory-related adverse events) associated with immunotherapies including checkpoint inhibitor therapies and cell based immunotherapies including CAR-T therapies.

BACKGROUND OF THE DISCLOSURE

It is estimated that metastases cause 90% of cancer-related deaths worldwide. In most cases, the metastatic tumour cells develop methods to evade immune responses and become resistant to therapy. Resistance to cancer treatment can be intrinsic to the tumour cells, but it is often conferred or augmented by non-malignant cells that make up the tumour microenvironment (TME). The TME is composed of tissue-resident cells, stromal cells, and other cells recruited by the tumor, and so it may include endothelial cells, pericytes, fibroblasts, mesenchymal stem cells, and a variety of immune cells, including regulatory T ($T_{reg}$) cells, mast cells, neutrophils, myeloid-derived suppressor cells, and tumor associated macrophages. These cells promote tumor angiogenesis, cancer cell invasion, and/or disrupt immune surveillance. Macrophages are among the most common type of tumor-associated cells. Researchers originally assumed that these immune cells were part of the body's response to reject tumours, and indeed a major check on the development of cancers is the immune system's surveillance and reaction to the presence of cancer, by cells of the innate immune system (e.g., macrophage, neutrophils) as well as cells associated with an adaptive immune response (e.g., T and B cells). However, in some cases, the cancer is able to evade and co-opt the immune system, so that rather than attacking the tumor, these immune system cells become part of the tumor's support and defense system. The immune TME can be modified to support the tumour and promote its progression while suppressing immune cell-mediated cytotoxicity. Substantial clinical and experimental evidence indicates that macrophages—present abundantly in most tumour types—have a major regulatory role in promoting tumour progression to malignancy. Macrophages in both primary tumors (tumor-associated macrophages or TAMs) and in metastatic tumors (metastasis-associated macrophages or MAMs) are abundant in most solid tumors and may be associated with tumor metastasis. Accumulation of TAMs, MAMs, and their progenitor cells is seemingly driven by chemokine ligands released by tumor and stromal cells. For example, there is evidence that TAMs and MAMs are derived at least in part from CCR2-expressing monocytes recruited by CCL2-expressing tumor cells and/or CCL2-expressing stromal cells. The precise mechanisms are not fully defined, however, and other CCR2 ligands such as CCL12, cytokines such as VEGF and CSF1, and other chemo-attractant signals such as CCL5-CCR5, CCL20-CCR6, CXCL12-CXCR4 may provide an alternative or additional chemoattractant pathway for recruitment of TAMs. Thus, efforts to target specific chemoattractant receptors or ligands, e.g., specifically blocking the CCR2-CCL2 interaction, have not been entirely effective, probably because the cancers are capable of exploiting alternative pathways.

Immune activation is primarily T-cell mediated and regulated by stimulatory, co-stimulatory, and inhibitory (checkpoint) signals. When T-cells, encounter a self-cell, there are important receptor-ligand interactions that provide a check on activation, so that the immune cells do not attack the body's normal cells. Cancer cells have genetic and epigenetic alterations which can result in antigen expression that can elicit an immune activation, but cancer cells can also exploit these immune checkpoint interactions, such as PD-1/PD-L1 and CTLA4/B7-1/B7-2, to deactivate the immune cells, rendering the immune system ineffective to destroy the cancer. Immune checkpoint inhibitors have been effective in many patients suffering from various types of cancers, as they allow destruction of the cancers by the patient's own immune system.

However, immunotherapy-related adverse events can limit the use of checkpoint blockade therapy and can result in serious adverse outcomes. Blocking the immune checkpoints can allow the immune system to attack normal tissue. This leads to inflammatory conditions such as dermatitis, colitis, arthritis, nephritis, myositis, polymyalgia-like syndromes, and cytokine release syndrome (CRS) caused by a large, rapid release of cytokines into the blood from immune cells affected by the immunotherapy. These side effects which can be very serious and occasionally fatal. Thus, in spite of its considerable benefit in patients with cancer, immune checkpoint blockade can be limited by the occurrence of immunotherapy-related adverse events.

Eleven families of phosphodiesterases (PDEs) have been identified but only PDEs in Family I, the Ca2+/calmodulin-dependent phosphodiesterases (CaM-PDEs), which are activated by Ca2+/calmodulin, have been shown to mediate the calcium dependent cyclic nucleotide (e.g. cGMP and cAMP) signaling pathways. The three known CaM-PDE genes, PDE1A, PDE1B, and PDE1C, are all expressed in central nervous system tissue. PDE1A is expressed in the brain, lung and heart. PDE1B is primarily expressed in the central nervous system, but it is also detected in monocytes and neutrophils and has been shown to be involved in inflammatory responses of these cells. PDE1C is expressed in olfactory epithelium, cerebellar granule cells, striatum, heart, vascular smooth muscle and tumor cells. PDE1C has been demonstrated to be a major regulator of smooth muscle proliferation in human smooth muscle. Cyclic nucleotide phosphodiesterases down-regulate intracellular cAMP and cGMP signaling by hydrolyzing these cyclic nucleotides to their respective 5'-monophosphates (5'ΔMP and 5'GMP), which are inactive in terms of intra-cellular signaling pathways. Both cAMP and cGMP are central intracellular second-messengers and they play roles in regulating numerous cellular functions. PDE1A and PDE1B preferentially hydrolyze cGMP over cAMP, while PDE1C shows approximately equal cGMP and cAMP hydrolysis.

There is a substantial need for a means of targeting multiple chemokine pathways involved in tumor recruitment of macrophages and other cells, a need for new therapies which complements and enhances checkpoint inhibitor therapies, and a need for a safe and selective strategy for mitigating the serious side effects (i.e., inflammatory-related adverse events) associated with checkpoint inhibitor therapies.

SUMMARY OF THE DISCLOSURE

The inventors have previously shown that inhibition of PDE1 activity using the presently disclosed compounds can safely restore cAMP function in a wide spectrum of pathological conditions, including models of neurodegeneration and neuroinflammation, heart failure, pulmonary hypertension and peripheral inflammation and in humans with certain diseases. More recently, the inventors have shown that PDE1 inhibitors obstruct cellular migration of microglia and monocytes. Recent evidence indicates that PDE1, particularly the PDE1C isoform, is over expressed in experimental tumor models such as melanoma, neuroblastoma, renal cell and colon carcinomas, and osteosarcoma. In addition, focal genomic over representation of PDE1C in Glioblastoma Multiforme (GBM) cells has been demonstrated. Genomic gain of PDE1C is associated with increased expression in GBM-derived cell cultures and is essential for driving cell proliferation, migration and invasion in cancer cells.

Many types of cancer cells over-express PDE1 activity, which is identified through various biomarkers, such as increased RNA expression, DNA copy number, PDE1 binding (PET or radio-isotope retention of PDE1 inhibitor molecules) or enzymatic activity. These cancer cells also exhibit low levels of cAMP, which can be increased by PDE1 inhibitors. Such characteristics can be treated with PDE-1 inhibitors alone or in combination with chemotherapeutics, gene therapeutics and/or immunologic approaches. Inhibiting of PDE1 provokes apoptotic cell death, prevents migration, limits metastasis, and reduces inflammation. In this way, PDE1 inhibitors are synergistic with chemotherapeutics and immunologic approaches.

The disclosure thus provides PDE1 inhibitors for use to inhibit recruitment of immune system cells, including macrophages and microglia, and other cells to the cancer, and to inhibit the metastasis, tumor angiogenesis and proliferation, cancer cell invasion, and disruption of immune surveillance provided by the recruited cells. PDE1 inhibits not only CCL2 but also other cytokines and chemokines believed to be involved in this recruitment and is therefore expected to be more effective than therapies such as monoclonal antibodies or other specific inhibitors of the CCR2-CCL2 interaction.

The disclosure also provides the use of PDE1 inhibitors in combination with cancer immunotherapies, including checkpoint inhibitor, genome editing and CAR-T therapies, the combinations of which should both enhance the effectiveness of the these therapies by reducing the interference with immune surveillance by TAMs and MAMs, as well as mitigating the inflammatory-related adverse events associated with checkpoint inhibitor therapies, such as cytokine release syndrome (CRS). PDE1 inhibition is useful prophylactically as well as therapeutically in these cases, and a PDE1 inhibitor may be administered together with other anti-inflammatory agents such as corticosteroids and antihistamines to prevent CRS and other inflammatory conditions resulting from checkpoint inhibitor therapies.

The combination of PDE1 inhibitor therapy, known to be anti-inflammatory, with immunostimulatory checkpoint inhibitor therapy may seem counter-intuitive, but it is nevertheless believed to be effective due to the dual effects of the PDE1 inhibitors (i) in inhibiting recruitment of protective cells, particularly macrophages, by the cancer, and (ii) in reducing the risk of cytokine release syndrome and other side effects of the checkpoint inhibitor therapy.

The disclosure also provides the use of a PDE1 inhibitor for the treatment of a cancer or tumor, including, e.g., carcinomas, melanomas, and astrocytomas. Moreover, impaired cAMP (or cGMP) levels may arise from overexpression of PDE1 isoforms in various cancer pathologies. Inhibition of selective PDE1 isoforms, which raises the levels of intracellular cAMP (and/or cGMP), induces apoptosis and cell cycle arrest in a broad spectrum of tumor cells and regulates the tumor microenvironment preventing cellular migration, inflammation, and tissue invasion. Therefore, the development and clinical application of inhibitors specific for individual PDE1 may selectively restore normal intracellular signaling, providing antitumor therapy with reduced adverse effects.

Previous studies have demonstrated that PDE1 (i.e., PDE1C) is significantly overexpressed in the tumor environment of glioblastoma patients compared to healthy patients (i.e., those not suffering from glioblastoma). siRNA mediated silencing of PDE1C has been shown to inhibit proliferation and invasion in patient-derived cell cultures of glioblastoma. Without being bound by any theory, inhibition of PDE1 may be effective in the therapeutic intervention of certain cancers or tumors, such as glioblastoma. Treating brain tumors in particular requires compounds possessing the ability to cross the blood brain barrier. The compounds of the present disclosure are potent inhibitors of PDE1. In particular the presently disclosed compounds show high selectivity for PDE1 and are capable of penetrating the blood brain barrier.

Therefore, in various embodiments, the present disclosure provides for methods of treating a condition selected from a cancer or tumor comprising administering a pharmaceutically acceptable amount of a PDE1 inhibitor as disclosed herein to a subject in need thereof. In some embodiments, the cancer or tumor is a glioma, leukemia, lymphoma, melanoma, neuroblastoma, carcinoma or osteosarcoma. In some embodiments, the cancer or tumor is an astrocytoma, such as glioblastoma multiforme. In some embodiments, the PDE1 inhibitor is administered in combination with an antitumor agent.

In various embodiments, the present disclosure provides for methods of inhibiting the proliferation, migration and/or invasion of tumorous cells comprising administering a pharmaceutically acceptable amount of a PDE1 inhibitor as disclosed herein to a subject in need thereof. In some embodiments, the cancer or tumor is a glioma, leukemia, melanoma, neuroblastoma, carcinoma or osteosarcoma. In some embodiments, the cancer or tumor is an astrocytoma, such as glioblastoma multiforme. In some embodiments, the PDE1 inhibitor is administered in combination with an antitumor agent.

In various embodiments, the present application provides for a method of treating a glioma comprising administering a pharmaceutically acceptable amount of a PDE1 inhibitor to a subject in need thereof. In some embodiments, the cancer or tumor is an astrocytoma, such as glioblastoma multiforme. In some embodiments, the PDE1 inhibitor is administered in combination with an antitumor agent.

In another aspect, the present disclosure also includes a PDE1 inhibitor of Formulas I, Ia, II, III, IV, V, and/or VI described hereinbelow in free or salt form. In a preferred embodiment, the PDE1 inhibitor is a selective PDE1 inhibitor. In another embodiment, the disclosure further provides a pharmaceutical composition comprising a PDE1 inhibitor in free or pharmaceutically acceptable salt form, in admixture with a pharmaceutically acceptable carrier.

In various embodiments, the present disclosure provides for combination therapies comprising a PDE1 inhibitor of Formulas I, Ia, II, III, IV, V, and/or VI described hereinbelow in free or salt form and an antitumor agent. The combination therapy can be used in conjunction with any of the methods disclosed herein. In some embodiments, the antitumor agent is administered concurrently with, before or after administration of the PDE1 inhibitor.

In various embodiments, the present disclosure also provides for pharmaceutical compositions comprising Compounds of the present disclosure prepared using conventional diluents or excipients and techniques known in the art. Thus, oral dosage forms may include tablets, capsules, solutions, suspensions and the like.

In various embodiments, the present disclosure also provides PDE1 inhibitors according to Formulas I, Ia, II, III, IV, V, and/or VI described hereinbelow in free or salt form for use in the treatment of a condition selected from a cancer or tumor, inhibiting the proliferation, migration and/or invasion of tumorous cells, or treating a glioma.

BRIEF DESCRIPTION OF THE DRAWINGS

FIG. 7A shows Chemotaxis towards 100 M ADP measured in a Boyden chamber system for 4 hrs. FIG. 7B shows dose dependent inhibition of ADP chemotaxis by P2RY12 inhibitors.

FIG. 8A shows cyclic AMP levels normalized to the vehicle value of pmol cAMP/number of cells. FIG. 8B shows levels of phosphorylation of VASP at serine 157 were as measured on a Western blot. The top graph shows phosphorylation and the bottom graph shows levels of total VASP. Insets show representative samples; the same samples were loaded on each blot in the order indicated in the bar graphs. Green bands are p-VASP (top) or total VASP (bottom). Samples were normalized to actin as a loading control (red bands).

DETAILED DESCRIPTION OF THE DISCLOSURE

Figure 1:
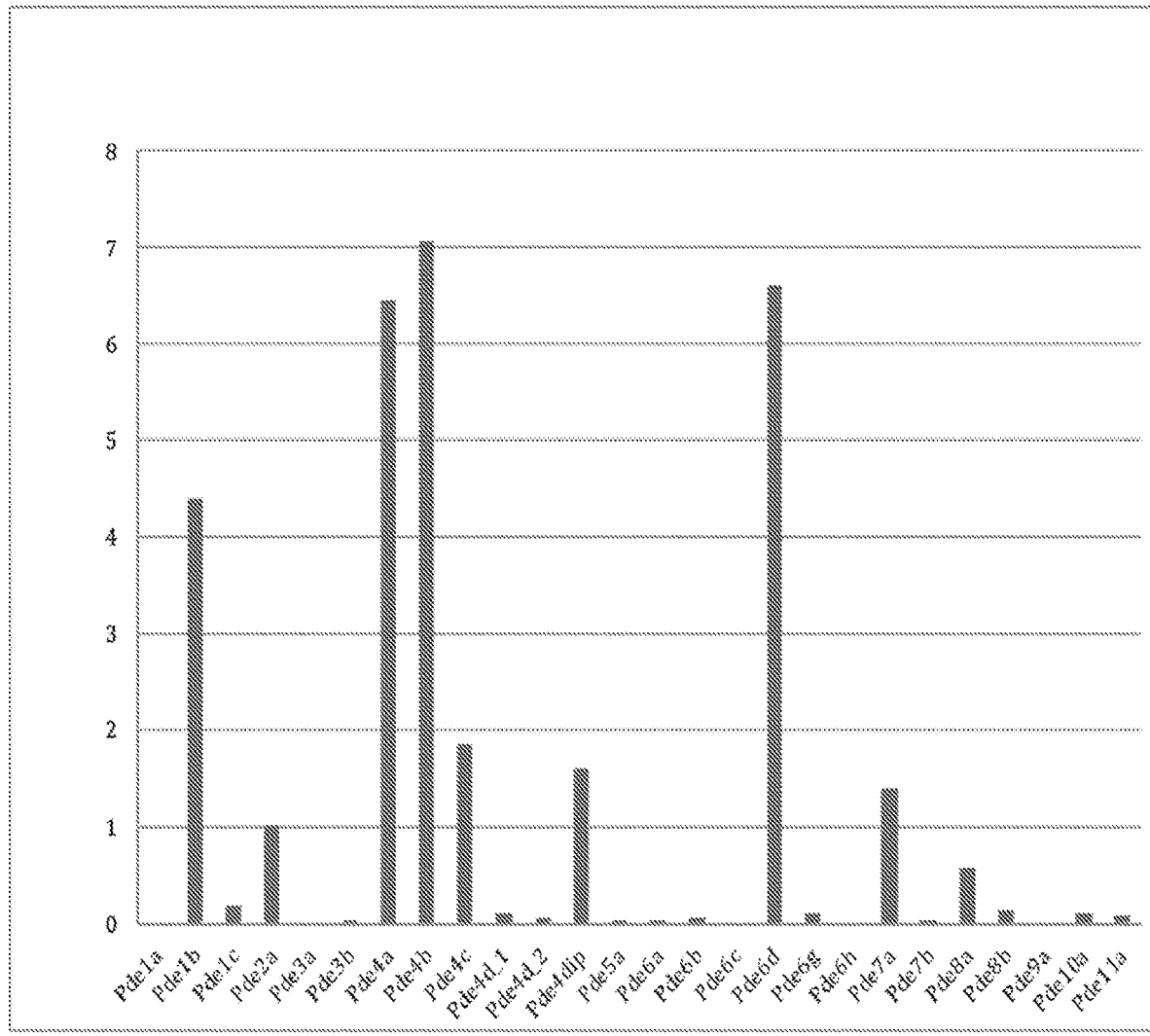
FIG. 1 depicts phosphodiesterase expression in BV2 cells treated with LPS-RNAseq analysis. FPKM refers to Fragment Reads per kilobase of exon per million reads mapped.

Compounds for Use in the Methods of the Disclosure

In one embodiment, the PDE1 inhibitors for use in the methods of treatment and prophylaxis described herein are selective PDE1 inhibitors.

PDE1 Inhibitors

In one embodiment the invention provides that the PDE1 inhibitors for use in the methods of treatment and prophylaxis described herein are compounds of Formula I:

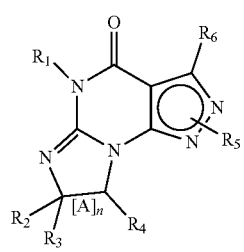

Formula I wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl; or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl;

or $R_5$ is attached to one of the nitrogens on the pyrazolo portion of Formula I
and is a moiety of Formula A

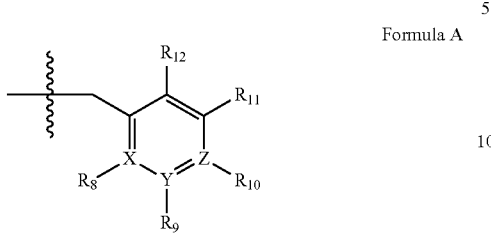

Formula A wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl) optionally substituted with halogen, or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylalkyl)amino (e.g., N-phenyl-N-(1,1'-biphen-4-yl-methyl)amino); and (v) n=0 or 1;

(vi) when n=1, A is $-C(R_{13}R_{14})-$
wherein $R_{13}$ and $R_{14}$, are, independently, H or $C_{1-4}$ alkyl, aryl, heteroaryl, (optionally hetero)arylalkoxy or (optionally hetero)arylalkyl;

in free, salt or prodrug form, including its enantiomers, diastereoisomers and racemates.

In another embodiment the invention provides that the PDE1 inhibitors for use in the methods of treatment and prophylaxis described herein are Formula 1a:

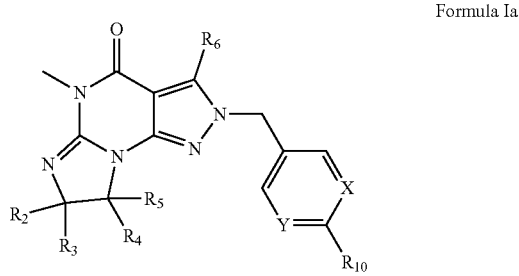

Formula Ia wherein
(i) $R_2$ and $R_5$ are independently H or hydroxy and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ and $R_5$ are each H; or $R_2$, $R_4$ and $R_5$ are H and $R_3$ is isopropyl [pref. the carbon carrying $R_3$ having the R configuration];

(ii) $R_6$ is (optionally halo-substituted) phenylamino, (optionally halo-substituted) benzylamino, $C_{1-4}$alkyl, or $C_{1-4}$alkyl sulfide; for example, phenylamino or 4-fluorophenylamino;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl (for example 6-fluoropyrid-2-yl), or thiadiazolyl (e.g., 1,2,3-thiadiazol-4-yl); and (iv) X and Y are independently C or N, in free, pharmaceutically acceptable salt or prodrug form, including its enantiomers, diastereoisomers and racemates.

In another embodiment the invention provides that the PDE1 inhibitors for use in the methods of treatment and prophylaxis described herein are compounds of Formula II:

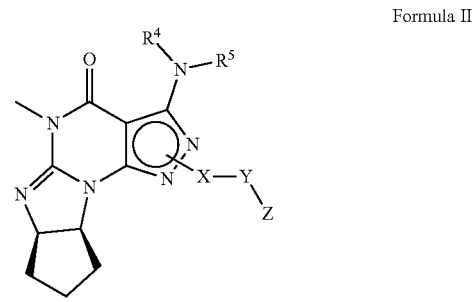

Formula II (i) X is $C_{1-6}$alkylene (e.g., methylene, ethylene or prop-2-yn-1-ylene);

(ii) Y is a single bond, alkynylene (e.g., $-C\equiv C-$), arylene (e.g., phenylene) or heteroarylene (e.g., pyridylene);

(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), $-C(O)-R^1$, $-N(R^2)(R^3)$, or $C_{3-7}$cycloalkyl optionally containing at least one atom selected from a group consisting of N or O (e.g., cyclopentyl, cyclohexyl, tetrahydro-2H-pyran-4-yl, or morpholinyl);

(iv) $R^1$ is $C_{1-6}$alkyl, halo$C_{1-6}$alkyl, OH or O$C_{1-6}$alkyl (e.g., OCH$_3$);

(v) $R^2$ and $R^3$ are independently H or $C_{1-6}$alkyl;

(vi) $R^4$ and $R^5$ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;

(vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl), in free, salt or prodrug form.

In yet another embodiment the invention provides that the PDE1 inhibitors for use in the methods of treatment and prophylaxis described herein are Formula III:

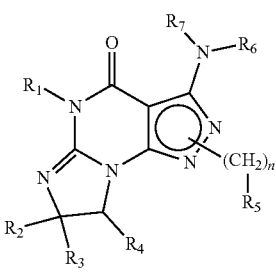

Formula III wherein
(i) $R_1$ is H or $C_{1-4}$ alkyl (e.g., methyl or ethyl);
(ii) $R_2$ and $R_3$ are independently H or $C_{1-6}$ alkyl (e.g., methyl or ethyl);
(iii) $R_4$ is H or $C_{1-4}$ alkyl (e.g., methyl or ethyl);
(iv) $R_5$ is aryl (e.g., phenyl) optionally substituted with one or more groups independently selected from —C(=O)—$C_{1-6}$ alkyl (e.g., —C(=O)—$CH_3$) and $C_{1-6}$-hydroxyalkyl (e.g., 1-hydroxyethyl);
(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl; and
(vi) n is 1, 2, 3, or 4,
in free or salt form.

In yet another embodiment the invention provides that the PDE1 inhibitors for use in the methods of treatment and prophylaxis described herein are Formula IV

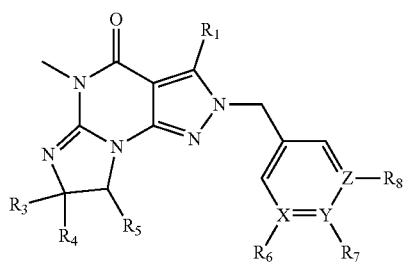

Formula IV in free or salt form, wherein
(i) $R_1$ is $C_{1-4}$alkyl (e.g., methyl or ethyl), or —NH($R_2$), wherein $R_2$ is phenyl optionally substituted with halo (e.g., fluoro), for example, 4-fluorophenyl;
(ii) X, Y and Z are, independently, N or C;
(iii) $R_3$, $R_4$ and $R_5$ are independently H or $C_{1-4}$alkyl (e.g., methyl); or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively),
(iv) $R_6$, $R_7$ and $R_8$ are independently:
H,
$C_{1-4}$alkyl (e.g., methyl),
pyrid-2-yl substituted with hydroxy, or
—S(O)$_2$—$NH_2$;

(v) Provided that when X, Y and/or Z are N, then $R_6$, $R_7$ and/or $R_8$, respectively, are not present; and when X, Y and Z are all C, then at least one of $R_6$, $R_7$ or $R_8$ is —S(O)$_2$—$NH_2$ or pyrid-2-yl substituted with hydroxy.

In another embodiment the invention provides that the PDE1 inhibitors for use in the methods as described herein are Formula V:

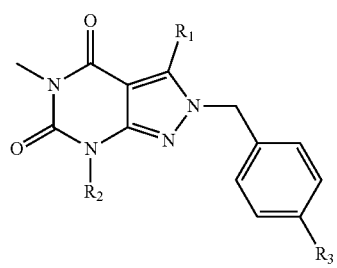

Formula V wherein
(i) $R_1$ is —NH($R_4$), wherein $R_4$ is phenyl optionally substituted with halo (e.g., fluoro), for example, 4-fluorophenyl;
(ii) $R_2$ is H or $C_{1-6}$alkyl (e.g., methyl, isobutyl or neopentyl);
(iii) $R_3$ is —SO$_2$NH$_2$ or —COOH;
in free or salt form.

In another embodiment the invention provides that the PDE1 inhibitors for use in the methods as described herein are Formula VI:

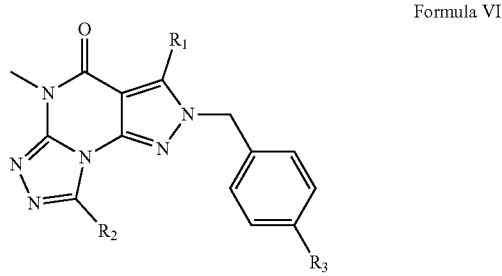

Formula VI wherein
(i) $R_1$ is —NH($R_4$), wherein $R_4$ is phenyl optionally substituted with halo (e.g., fluoro), for example, 4-fluorophenyl;
(ii) $R_2$ is H or $C_{1-6}$alkyl (e.g., methyl or ethyl);
(iii) $R_3$ is H, halogen (e.g., bromo), $C_{1-6}$alkyl (e.g., methyl), aryl optionally substituted with halogen (e.g., 4-fluorophenyl), heteroaryl optionally substituted with halogen (e.g., 6-fluoropyrid-2-yl or pyrid-2-yl), or acyl (e.g., acetyl),
in free or salt form.

In one embodiment, the present disclosure provides for administration of a PDE1 inhibitor for use in the methods described herein (e.g., a compound according to Formulas I, Ia, II, III, IV, V, and/or VI), wherein the inhibitor is a compound according to the following:

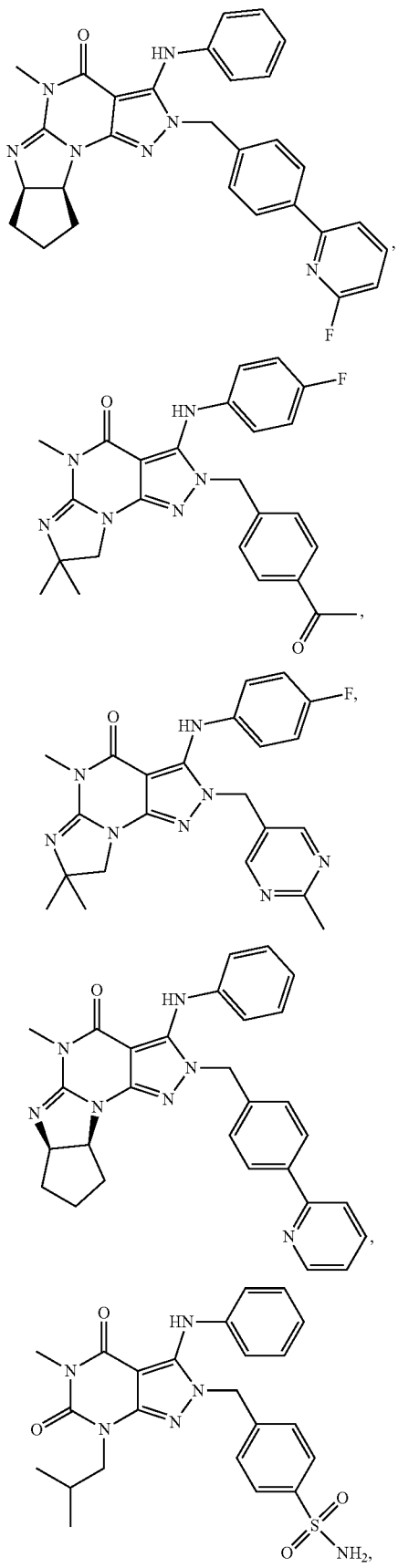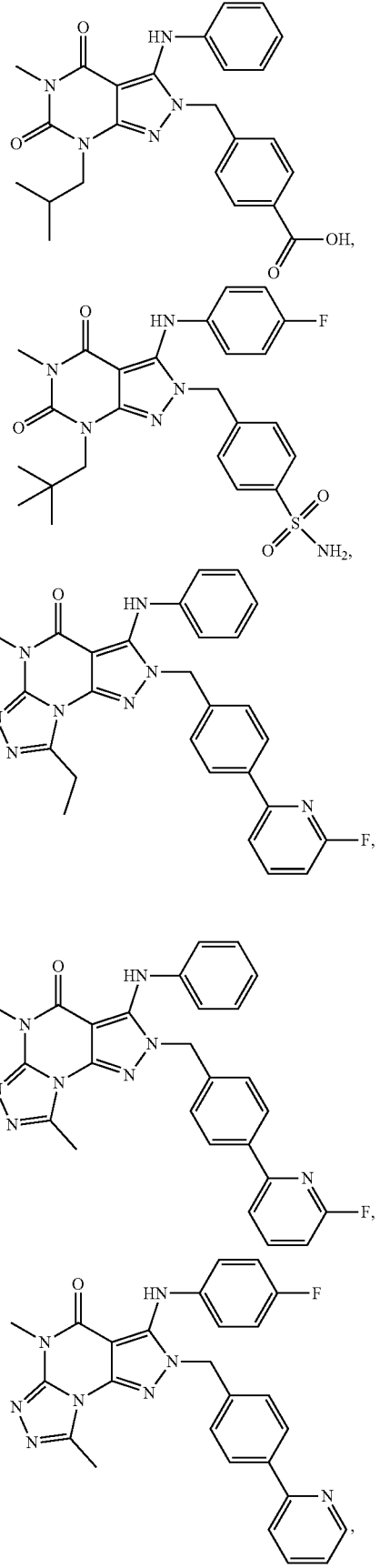

13
-continued
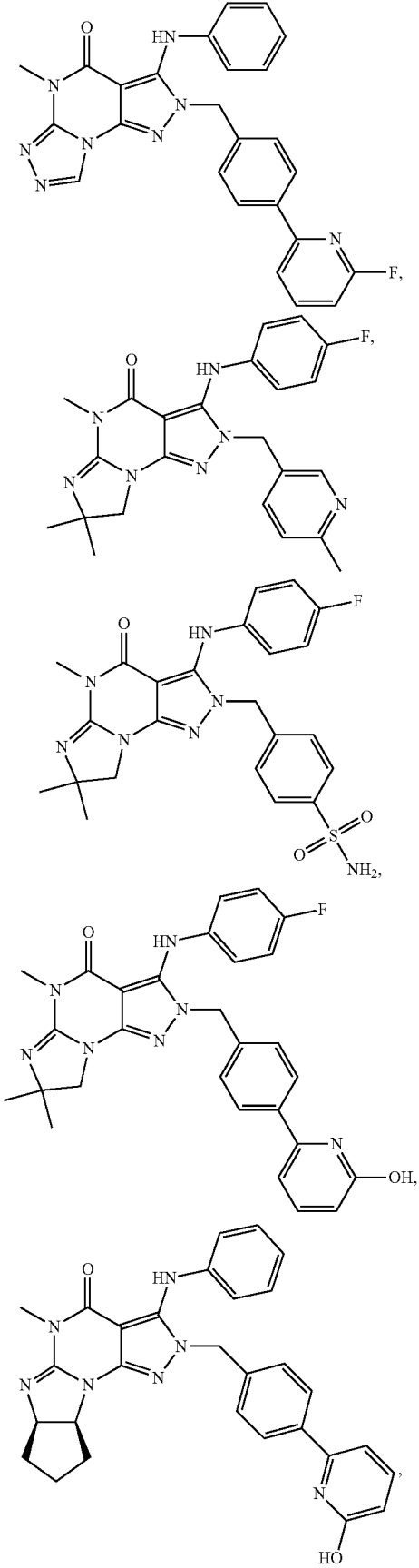
14
-continued
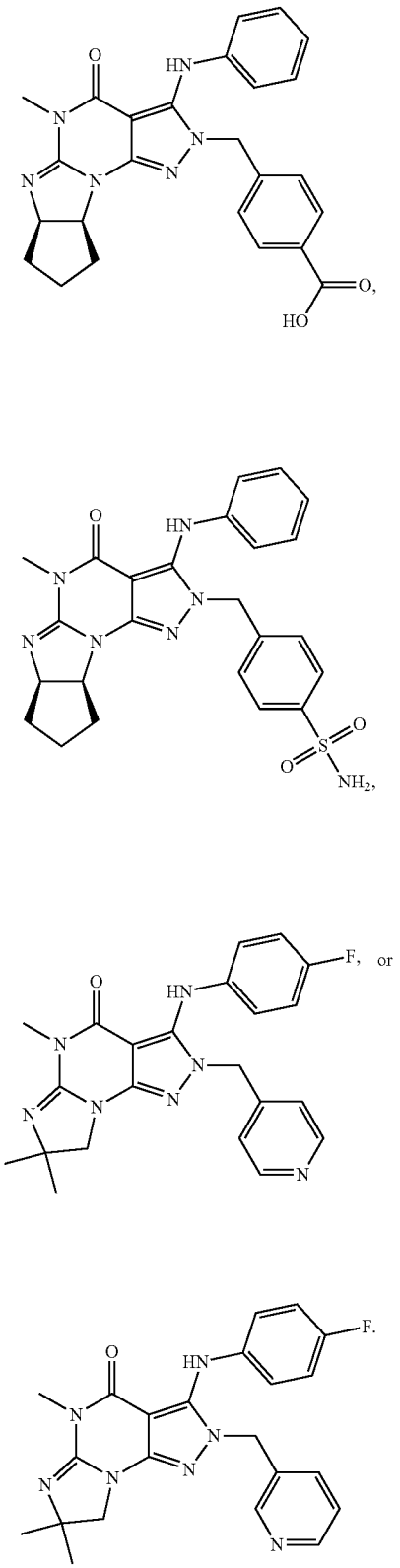
In one embodiment the invention provides administration of a PDE1 inhibitor for treatment or prophylaxis as described herein, wherein the inhibitor is a compound according to the following:

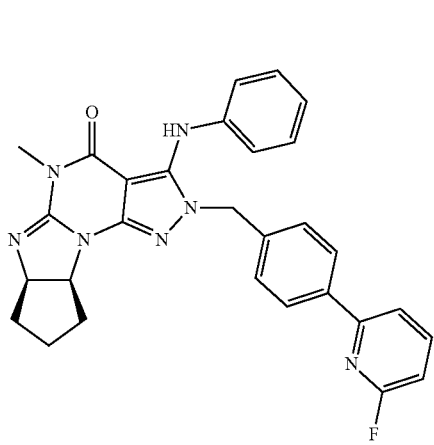 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

In still another embodiment, the invention provides administration of a PDE1 inhibitor for treatment or prophylaxis as described herein, wherein the inhibitor is a compound according to the following:

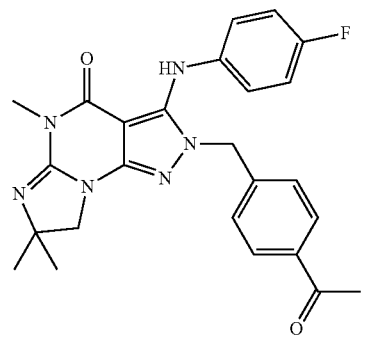 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

In still another embodiment, the invention provides administration of a PDE1 inhibitor for treatment or prophylaxis as described herein, wherein the inhibitor is a compound according to the following:

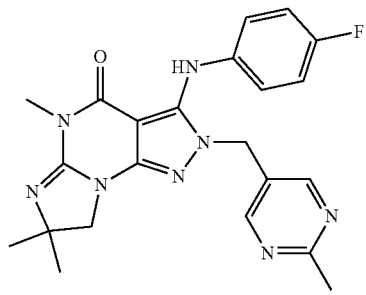 [SMILES: Cc1ncc(Cn2nc3c(c2Nc2ccc(F)cc2)C(=O)N(C)C2=NC(C)(C)CN23)cn1]

in free or pharmaceutically acceptable salt form.

In still another embodiment, the invention provides administration of a PDE1 inhibitor for treatment or prophylaxis as described herein, wherein the inhibitor is a compound according to the following:

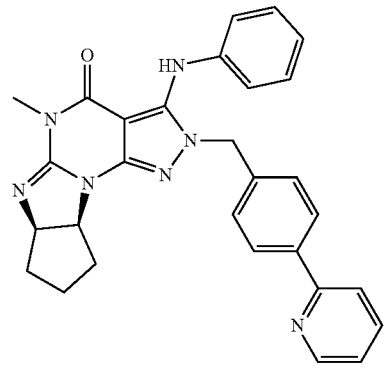 [SMILES: CN1C(=O)c2c(nn(Cc3ccc(-c4ccccn4)cc3)c2Nc2ccccc2)N2C1=N[C@@H]1CCC[C@@H]12]

in free or pharmaceutically acceptable salt form.

In one embodiment, selective PDE1 inhibitors of the any of the preceding formulae (e.g., Formulas I, Ia, II, III, IV, V, and/or VI) are compounds that inhibit phosphodiesterase-mediated (e.g., PDE1-mediated, especially PDE1B-mediated) hydrolysis of cGMP, e.g., the preferred compounds have an $IC_{50}$ of less than 1 μM, preferably less than 500 nM, preferably less than 50 nM, and preferably less than 5 nM in an immobilized-metal affinity particle reagent PDE assay, in free or salt form.

In other embodiments, the invention provides administration of a PDE1 inhibitor for treatment of a condition selected from a cancer or tumor; for inhibiting the proliferation, migration and/or invasion of tumorous cells; and/or for treating a glioma, wherein the inhibitor is a compound according to the following:

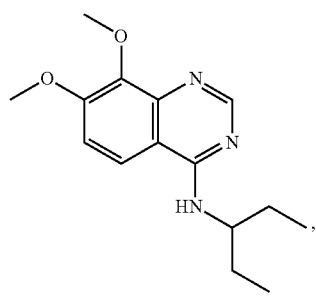

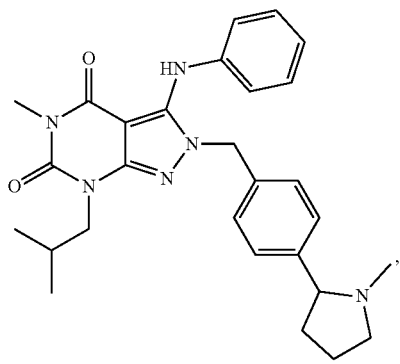

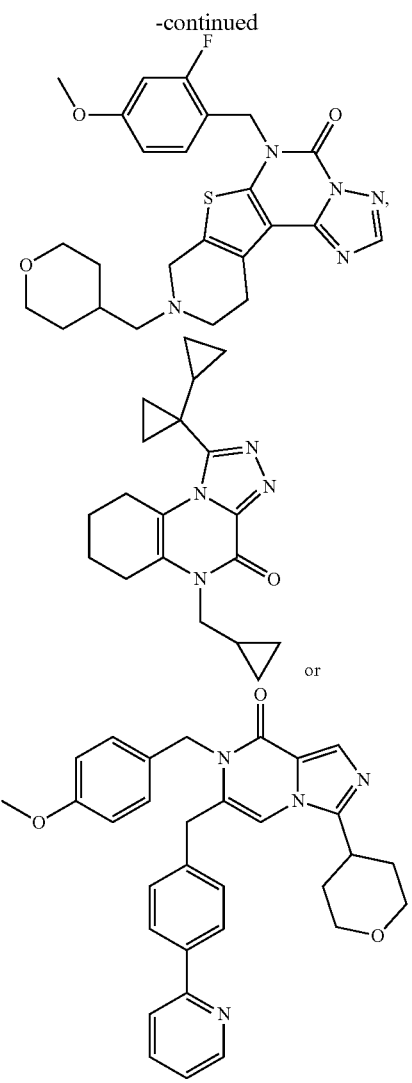

in free or pharmaceutically acceptable salt form.

Further examples of PDE1 inhibitors suitable for use in the methods and treatments discussed herein can be found in International Publication WO2006133261A2; U.S. Pat. Nos. 8,273,750; 9,000,001; 9,624,230; International Publication WO2009075784A1; U.S. Pat. Nos. 8,273,751; 8,829,008; 9,403,836; International Publication WO2014151409A1, U.S. Pat. Nos. 9,073,936; 9,598,426; 9,556,186; U.S. Publication 2017/0231994A1, International Publication WO2016022893A1, and U.S. Publication 2017/0226117A1, each of which are incorporated by reference in their entirety.

Still further examples of PDE1 inhibitors suitable for use in the methods and treatments discussed herein can be found in International Publication WO2018007249A1; U.S. Publication 2018/0000786; International Publication WO2015118097A1; U.S. Pat. No. 9,718,832; International Publication WO2015091805A1; U.S. Pat. No. 9,701,665; U.S. Publication 2015/0175584A1; U.S. Publication 2017/0267664A1; International Publication WO2016055618A1; U.S. Publication 2017/0298072A1; International Publication WO2016170064A1; U.S. Publication 2016/0311831A1; International Publication WO2015150254A1; U.S. Publication 2017/0022186A1; International Publication WO2016174188A1; U.S. Publication 2016/0318939A1; U.S. Publication 2017/0291903A1; International Publication WO2018073251A1; International Publication WO2017178350A1; U.S. Publication 2017/0291901A1; International Publication WO2018/115067; U.S. Publication 2018/0179200A; U.S. Publication US20160318910A1; U.S. Pat. No. 9,868,741; International Publication WO2017/139186A1; International Application WO2016/040083; U.S. Publication 2017/0240532; International Publication WO 2016033776A1; U.S. Publication 2017/0233373; International Publication WO2015130568; International Publication WO2014159012; U.S. Pat. Nos. 9,034,864; 9,266,859; International Publication WO2009085917; U.S. Pat. No. 8,084,261; International Publication WO2018039052; U.S. Publication US20180062729; and International Publication WO2019027783 each of which are incorporated by reference in their entirety. In any situation in which the statements of any documents incorporated by reference contradict or are incompatible with any statements made in the present disclosure, the statements of the present disclosure shall be understood as controlling.

Methods of treatment with PDE1 inhibitors of the present disclosure are further disclosed in U.S. provisional application 62/676,638, filed on May 25, 2018, and U.S. provisional application 62/688,641, filed Jun. 22, 2018, both of which are incorporated herein by reference in their entirety; and by International Publication WO2018049417A1, also incorporated by reference herein.

If not otherwise specified or clear from context, the following terms herein have the following meanings:

a. "Selective PDE1 inhibitor" as used herein refers to a PDE1 inhibitor with at least 100-fold selectivity for PDE1 inhibition over inhibition of any other PDE isoform.

b. "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

c. "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

d. "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

e. "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

f. "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

Compounds of the Disclosure, e.g., PDE1 inhibitors as described herein, may exist in free or salt form, e.g., as acid addition salts. In this specification unless otherwise indicated, language such as "Compounds of the Disclosure" is to be understood as embracing the compounds in any form, for example free or acid addition salt form, or where the compounds contain acidic substituents, in base addition salt form. The Compounds of the Disclosure are intended for use as pharmaceuticals, therefore pharmaceutically acceptable salts are preferred. Salts which are unsuitable for pharmaceutical uses may be useful, for example, for the isolation or purification of free Compounds of the Disclosure or their pharmaceutically acceptable salts, are therefore also included.

Compounds of the Disclosure may in some cases also exist in prodrug form. A prodrug form is compound which converts in the body to a Compound of the Disclosure. For example, when the Compounds of the Disclosure contain hydroxy or carboxy substituents, these substituents may form physiologically hydrolysable and acceptable esters. As used herein, "physiologically hydrolysable and acceptable ester" means esters of Compounds of the Disclosure which are hydrolysable under physiological conditions to yield acids (in the case of Compounds of the Disclosure which have hydroxy substituents) or alcohols (in the case of Compounds of the Disclosure which have carboxy substituents) which are themselves physiologically tolerable at doses to be administered. Therefore, wherein the Compound of the Disclosure contains a hydroxy group, for example, Compound-OH, the acyl ester prodrug of such compound, i.e., Compound-O—C(O)—C1-4alkyl, can hydrolyze in the body to form physiologically hydrolysable alcohol (Compound-OH) on the one hand and acid on the other (e.g., HOC(O)—C1-4alkyl). Alternatively, wherein the Compound of the Disclosure contains a carboxylic acid, for example, Compound-C(O)OH, the acid ester prodrug of such compound, Compound-C(O)O—C1-4alkyl can hydrolyze to form Compound-C(O)OH and HO—C1-4alkyl. As will be appreciated the term thus embraces conventional pharmaceutical prodrug forms.

In another embodiment, the disclosure further provides a pharmaceutical composition comprising a PDE1 inhibitor in combination with an antitumor agent, each in free or pharmaceutically acceptable salt form, in admixture with a pharmaceutically acceptable carrier. The term "combination," as used herein, embraces simultaneous, sequential, or contemporaneous administration of the PDE1 inhibitor and the antitumor agent. In another embodiment, the disclosure provides a pharmaceutical composition containing such a compound. In some embodiments, the combination of the PDE1 inhibitor and the antitumor agent allows the antitumor agent to be administered in a dosage lower than would be effective if administered as sole monotherapy.

Methods of Using Compounds of the Disclosure

In one embodiment, the present application provides for a method (Method 1) of treating a cancer or tumor by inhibiting
  a. cancer or tumor recruitment of immune cells, e.g., macrophages (e.g., TAMs or MAMs) and/or microglia, e.g., chemokine-mediated recruitment, e.g., CCL2-mediated recruitment;
  b. tumor or cancer metastasis, e.g., TAM- or MAM-associated metastasis;
  c. tumor or cancer angiogenesis, e.g., TAM- or MAM-associated angiogenesis;
  d. disruption of immune surveillance, e.g., e.g., TAM- or MAM-associated disruption of immune surveillance of a tumor or cancer; comprising administering a pharmaceutically acceptable amount of a PDE1 inhibitor (e.g., PDE1 inhibitor according to Formulas I, Ia, II, III, IV, V, and/or VI), optionally in combination or association with a checkpoint inhibitor, to a subject in need thereof.

1.1 Method 1, wherein the cancer or tumor has elevated expression of PDE1.
1.2 Any preceding method, wherein the method comprises a method of inhibiting tumor recruitment of immune cells.
1.3 Any preceding method wherein the method comprises a method of inhibiting tumor recruitment of macrophages and/or microglia.
1.4 Any preceding method wherein the method comprises a method of inhibiting tumor recruitment of macrophages and/or microglia, wherein the recruitment is mediated at least in part by elevated expression of CCL2 by tumor cells and/or cells in the tumor microenvironment.
1.5 Any preceding method wherein the method comprises a method of inhibiting tumor metastasis.
1.6 Any preceding method wherein the method comprises a method of inhibiting tumor angiogenesis.
1.7 Any preceding method wherein the method comprises a method of inhibiting disruption of immune surveillance of the tumor.
1.8 Any of the preceding methods, wherein the cells of the cancer or tumor exhibit one or more of increased PDE1 RNA expression, DNA copy number, PDE1 binding (e.g., PET or radio-isotope retention of PDE1 inhibitor molecules), modification to the PDE1 enzyme (i.e., truncation of the receptor leading to loss of calcium/calmodulin control), or PDE1 enzymatic activity (e.g., as measured in an enzymatic assay or as reflected in low levels of cAMP in the cancer cells or subcellular domain, e.g. microtubule domains, of the cancer cells) relative to normal cells of the same tissue type as the cancer cells.
1.9 Any preceding method, wherein the subject has a tumor.
1.10 Any preceding Method, wherein the subject has a tumor or cancer selected from one or more of acoustic neuroma, astrocytoma, chordoma, lymphoma (e.g., CNS lymphoma, Hodgkin's lymphoma or non-Hodgkin's lymphoma), craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid, Merkel cell carcinoma, colon carcinoma), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant schwannoma, malignant pheochromocytoma, malignant paraganglioma, melanoma, mercell cell neoplasm, cystosarcoma phylloides, or Wilms tumor.

1.11 Any preceding method, wherein the subject has a glioma, osteosarcoma, melanoma, leukemia, lymphoma, carcinoma or neuroblastoma.

1.12 Any preceding method, wherein the subject has a glioma (e.g., ependymoma, astrocytoma, oligodendrogliomas, brain stem glioma, optic nerve glioma, or mixed gliomas, e.g., oligoastrocytomas).

1.13 Any preceding method, wherein the subject has an astrocytoma (e.g., glioblastoma multiforme).

1.14 Any preceding method, wherein the subject has a glioblastoma multiforme.

1.15 Any preceding method, wherein the subject has a lymphoma.

1.16 Any preceding method, wherein the subject has lung cancer, pancreatic cancer, prostate cancer, urothelial cancer, cancers of the head and neck, or leukemia.

1.17 Any preceding method wherein the subject has a lymphocytic leukemia or a myelogenous leukemia.

1.18 Any preceding method wherein the subject has a cancer of the kidney, ureter, bladder or urethra.

1.19 Any preceding method, comprising administration of the PDE1 inhibitor to a patient receiving or scheduled to receive an immune checkpoint inhibitor, e.g. an inhibitor of CTLA-4, PD-1 and/or PD-L1.

1.20 Any preceding method, comprising administration of the PDE1 inhibitor to a patient receiving or scheduled to receive an immune checkpoint inhibitor selected from one or more members selected from nivolumab, pembrolizumab, cemiplimab, ipilimumab, avelumab, durvalumab, atezolizumab, spartalizumab.

1.21 Any preceding method, comprising administration of the PDE1 inhibitor to a patient receiving or scheduled to receive an inhibitor of CTLA-4.

1.22 Any preceding method, comprising administration of the PDE1 inhibitor to a patient receiving or scheduled to receive an inhibitor of PD-1.

1.23 Any preceding method, comprising administration of the PDE1 inhibitor to a patient receiving or scheduled to receive an inhibitor of PD-L1.

1.24 Any preceding method, wherein an immune checkpoint inhibitor is administered concurrently with the PDE1 inhibitor.

1.25 Any preceding method, wherein an immune checkpoint inhibitor is administered prior to administering the PDE1 inhibitor.

1.26 Any preceding method, wherein an immune checkpoint inhibitor is administered after administering the PDE1 inhibitor.

1.27 Any of the preceding methods, wherein the subject in need thereof was previously or concurrently administered a checkpoint inhibitor therapy.

1.28 Any of the preceding methods, wherein the subject in need thereof is suffering from a disease, disorder or adverse effect of immune checkpoint inhibitor therapy.

1.29 Any preceding method, wherein the subject is suffering from an inflammatory-related disorder consequent to immune checkpoint inhibitor therapy.

1.30 Any preceding method wherein the subject is suffering from, or at risk of suffering from, a side effect of immune checkpoint inhibitor therapy, e.g., wherein the side effect is selected from a systemic inflammatory response, a gastrointestinal inflammation-related disorder, an endocrine inflammation-related disorder, a dermatologic inflammation-related disorder, an ophthalmologic inflammation-related disorder, a neurologic inflammation-related disorder, a hematologic inflammation-related disorder, a genitourinary inflammation-related disorder, a respiratory inflammation-related disorder, a musculoskeletal inflammation-related disorder, a cardiac inflammation-related disorder, or a defined systemic inflammation-related disorder.

1.31 Any preceding method wherein the subject is suffering from a side effect of immune checkpoint inhibitor therapy, wherein the side effect is a gastrointestinal inflammation-related disorder, e.g., selected from colitis, enterocolitis, colitis complicated by intestinal perforation, hepatitis, and pancreatitis.

1.32 Any preceding method wherein the subject is suffering from a side effect of immune checkpoint inhibitor therapy, wherein the side effect is endocrine inflammation-related disorder, e.g., selected from hypophysitis (e.g., manifested as panhypopituitarism), thyrotoxicosis, hypothyroidism, syndrome of inappropriate secretion of antidiuretic hormone, central adrenal insufficiency, primary adrenal insufficiency, and diabetes mellitus.

1.33 Any preceding method wherein the subject is suffering from a side effect of immune checkpoint inhibitor therapy, wherein the side effect is a dermatologic inflammation-related disorder, e.g., selected from a rash, pruritis, vitiligo, dermatitis, sweet syndrome, drug eruption, poliosis, delayed hypersensitivity reaction, alopecia universalis, grover disease, pyoderma gangrenosum, toxic epidermal necrolysis, chronic non-caseation granuloma, bullous pemphigoid, and psoriasis.

1.34 Any preceding method wherein the subject is suffering from a side effect of immune checkpoint inhibitor therapy, wherein the side effect is an ophthalmologic inflammation-related disorder, e.g., selected from uveitis, conjunctivitis, orbital inflammation, Grave's ophthalmology, choroidal neovascularization, optic neuropathy, keratitis, and retinopathy.

1.35 Any preceding method wherein the subject is suffering from a side effect of immune checkpoint inhibitor therapy, wherein the side effect is a neurologic inflammation-related disorder, e.g., selected from encephalopathy, Guillan-Barre syndrome, polyradiculoneuropathy, symmetrical multifocal neuropathy, transverse myelitis, necrotizing myelopathy, myasthenia gravis, phrenic nerve palsy, immune related meningitis, meningioradiculoneuritis, peripheral neuropathy, autoimmune inner ear disease, multiple sclerosis, and inflammatory enteric neuropathy.

1.36 Any preceding method wherein the subject is suffering from a side effect of immune checkpoint inhibitor therapy, wherein the side effect is a hematologic inflammation-related disorder, e.g., selected from thrombocytopenia, pancytopenia, neutropenia, eosinophilia, pure red blood cell aplasia, acquired hemophilia A, and disseminated intravascular coagulopathy.

1.37 Any preceding method wherein the subject is suffering from a side effect of immune checkpoint inhibitor therapy, wherein the side effect is a genitourinary inflammation-related disorder, e.g., selected from renal failure, acute/granulomatous interstitial nephritis, acute tubular necrosis, and lymphotic vasculitis (e.g., lymphotic vasculitis of the uterus).

1.38 Any preceding method wherein the subject is suffering from a side effect of immune checkpoint inhibitor therapy, wherein the side effect is a respiratory inflammation-related disorder, e.g., selected from pneumonitis and acute respiratory distress.

1.39 Any preceding method wherein the subject is suffering from a side effect of immune checkpoint inhibitor therapy, wherein the side effect is a musculoskeletal inflammation-related disorder, e.g., selected from polyarthritis, athralgia, myalgia, chronic granulomatous inflammation of rectus abdominis muscle, and rhabdomyolysis.

1.40 Any preceding method wherein the subject is suffering from a side effect of immune checkpoint inhibitor therapy, wherein the side effect is a cardiac inflammation-related disorder, e.g., selected from precarditis and takotsubo like syndrome.

1.41 Any preceding method wherein the subject is suffering from a side effect of immune checkpoint inhibitor therapy, wherein the side effect is a systemic inflammation-related disorder, e.g. selected from lung sarcoidosis, cutaneous and pulmonary sarcoidosis, polymyalgia rheumatica, giant cell arteritis, muscular sarcoidosis, neurological and pulmonary sarcoidosis, celiac disease, lupus nephritis, dermamyositis, autoimmune inflammatory myopathy, and Vogt-Koyanagi like syndrome.

1.42 Any of the preceding methods, wherein the PDE1 inhibitor is administered before, after or in conjunction with radiation therapy and/or chemotherapy.

1.43 Any of the preceding methods, wherein the PDE1 inhibitor is administered concurrently with radiation therapy and/or chemotherapy.

1.44 Any of the preceding methods, wherein the PDE1 inhibitor is administered prior to radiation therapy and/or chemotherapy.

1.45 Any of the preceding methods, wherein the PDE1 inhibitor is administered after radiation therapy and/or chemotherapy.

1.46 Any of the preceding methods, wherein the PDE1 inhibitor is administered together with an additional antitumor agent, chemotherapeutic, gene therapeutic and/or immunologic treatment.

1.47 Any of the preceding methods, wherein the PDE1 inhibitor is a PDE1 inhibitor according to Formulas I, Ia, II, III, IV, V, and/or VI or a compound according to the following:

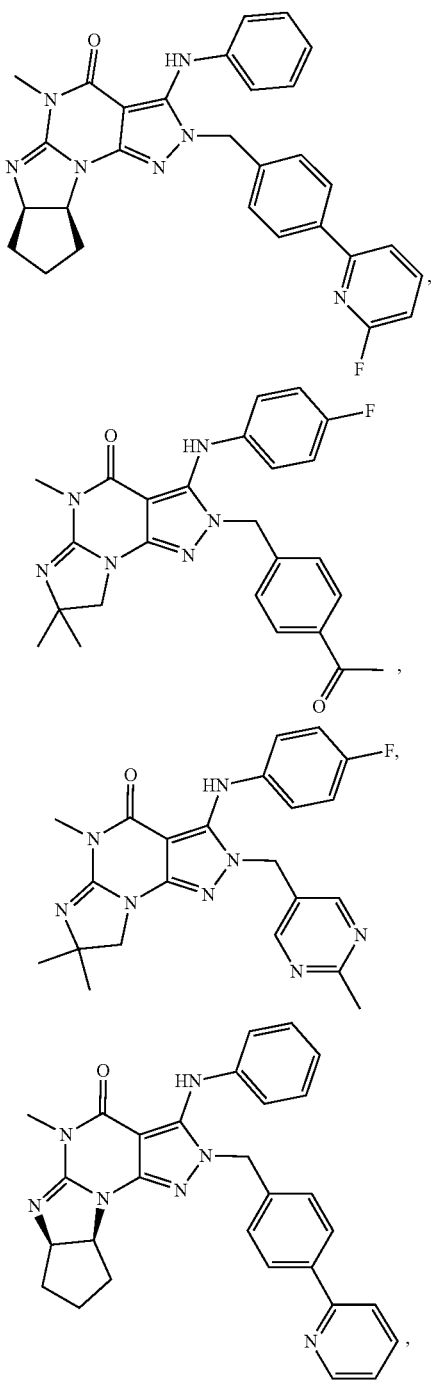

-continued

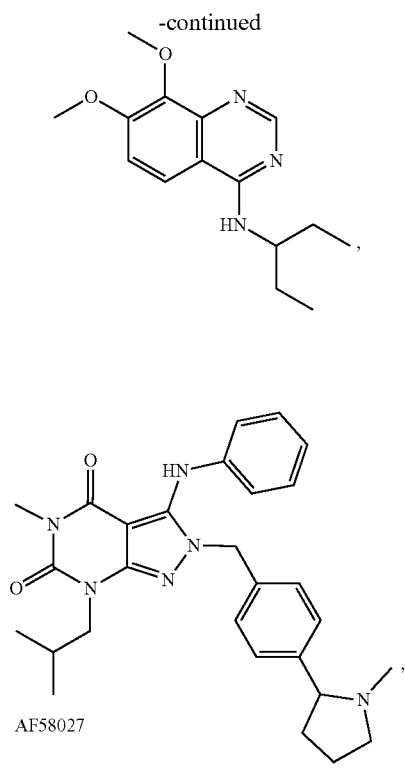

AF58027

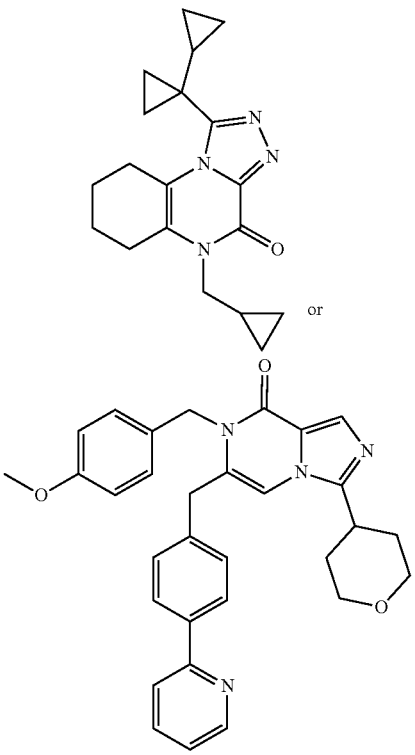

or in free or pharmaceutically acceptable salt form.

1.48 Any of the preceding methods, wherein the PDE1 inhibitor is a PDE1 inhibitor according to Formula Ia.

1.49 Any of the preceding methods, wherein the PDE1 inhibitor is a compound as follows:

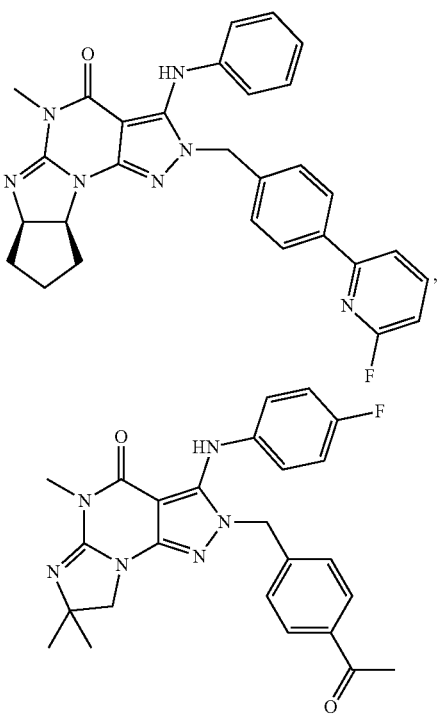

in free or pharmaceutically acceptable salt form.

1.50 Any of the preceding methods, wherein the PDE1 inhibitor is a compound as follows:

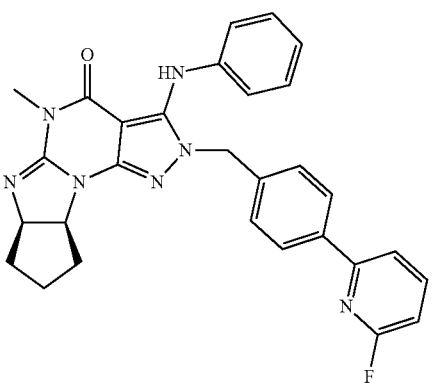 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form, e.g., in monophosphate salt form.

1.51 Any of the preceding methods, wherein the PDE1 inhibitor suppresses macrophage or microglia recruitment to metastatic cells.

1.52 Any of the preceding methods, wherein the PDE1 inhibitor suppresses the macrophage or microglia recruitment to metastatic cells mediated by CCL2.

1.53 Any preceding methods which is a method of treating a cancer or tumor comprising (i) administering a pharmaceutically acceptable amount of a PDE1 inhibitor (e.g., a PDE1 inhibitor according to Formulas I, Ia, II, III, IV, V, and/or VI), and (ii) administering a pharmaceutically acceptable amount of a checkpoint inhibitor, to a subject in need thereof.

1.54 Any of the preceding methods, further comprising administering a pharmaceutically acceptable amount of a beta blocker to the subject.

1.55 Any of the preceding methods, comprising administration of the PDE1 inhibitor to a patient receiving or scheduled to receive an immunotherapy (e.g., checkpoint inhibitor and/or CAR-T therapy).

1.56 The preceding method, wherein the immunotherapy is a CAR-T therapy.

In another embodiment, the disclosure provides a PDE1 inhibitor for use to inhibit (i) cancer or tumor recruitment of immune cells, e.g., macrophages (e.g., TAMs or MAMs) and/or microglia, e.g., chemokine-mediated recruitment, e.g., CCL2-mediated recruitment;

(ii) tumor or cancer metastasis, e.g., TAM- or MAM-associated metastasis;

(iii) tumor or cancer angiogenesis, e.g., TAM- or MAM-associated angiogenesis;

(iv) disruption of immune surveillance, e.g., e.g., TAM- or MAM-associated disruption of immune surveillance of a tumor or cancer; e.g., for use in any of Methods 1, et seq.

In another embodiment, the present application provides for a method (Method 2) of prophylaxis or mitigation of a disease, disorder or adverse effect consequent to administration of a checkpoint inhibitor therapy, the method comprising administering a pharmaceutically acceptable amount of a PDE1 inhibitor (i.e., PDE1 inhibitor according to Formulas I, Ia, II, III, IV, V, and/or VI) to a subject in need thereof.

2.1 Method 2, wherein the subject is administered the checkpoint inhibitor therapy is administered as a treatment for a tumor or cancer.

2.2 The preceding method, wherein the tumor or cancer exhibits increased expression of PDE1 in the cancerous or tumorous cells.

2.3 Any of methods 2.1-2.2, wherein the cancerous or tumorous cells exhibit increased expression of PDE1C in the cancerous or tumorous cells.

2.4 Any of methods 2.1-2.3, wherein the cancer cells exhibit one or more of increased PDE1 RNA expression, DNA copy number, PDE1 binding (e.g., PET or radio-isotope retention of PDE1 inhibitor molecules), modification to the PDE1 enzyme (e.g., truncation of the receptor leading to loss of calcium/calmodulin control), or PDE1 enzymatic activity (e.g., as measured in an enzymatic assay or as reflected in low levels of cAMP in the cancer cells or subcellular domain, e.g. microtubule domains, of the cancer cells) relative to normal cells of the same tissue type as the cancer cells.

2.5 Any of methods 2.1-2.4, wherein the condition is a tumor.

2.6 Any of methods 2.1-2.5, wherein the tumor is selected from one or more of acoustic neuroma, astrocytoma, chordoma, CNS lymphoma, craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid, Merkel cell carcinoma, colon carcinoma), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant schwannoma, malignant pheochromocytoma, malignant paraganglioma, melanoma, mer-cell cell neoplasm, cystosarcoma phylloides, or Wilms tumor.

2.7 Any of methods 2.1-2.6, wherein the tumor or cancer is a glioma, lymphoma, osteosarcoma, melanoma, leukemia, or neuroblastoma.

2.8 Any of methods 2.1-2.7, wherein the tumor or cancer is a glioma (e.g., ependymoma, astrocytoma, oligodendrogliomas, brain stem glioma, optic nerve glioma, or mixed gliomas, e.g., oligoastrocytomas).

2.9 The previous method, wherein the glioma is an astrocytoma (e.g., glioblastoma multiforme).

2.10 Any of methods 2.1-2.9, wherein the tumor or cancer is glioblastoma multiforme or a lymphoma.

2.11 Method 2.1, wherein the condition is a cancer.

2.12 Any of Methods 2.1 or 2.11, wherein the condition is a lung cancer, pancreatic cancer, prostate cancer, a urothelial cancer, cancers of the head and neck, or leukemia.

2.13 Method 2.12, wherein the leukemia is a lymphocytic leukemia or a myelogenous leukemia.

2.14 Method 2.12, wherein the urothelial cancer is a cancer of the kidney, ureter, bladder or urethra.

2.15 Any preceding method, wherein the checkpoint inhibitor is an inhibitor of CTLA-4, PD-1 and/or PD-L1.

2.16 Any preceding method, wherein the checkpoint inhibitor comprises one or more members selected from nivolumab, pembrolizumab, cemiplimab, ipilimumab, avelumab, durvalumab, atezolizumab, spartalizumab.

2.17 Any preceding method, wherein the checkpoint inhibitor is an inhibitor of CTLA-4.

2.18 Any of methods 2-2.16, wherein the checkpoint inhibitor is an inhibitor of PD-1.

2.19 Any of methods 2-2.16, wherein the checkpoint inhibitor is an inhibitor of PD-L1.

2.20 Any preceding method, wherein the checkpoint inhibitor is administered concurrently with the PDE1 inhibitor.

2.21 Any preceding method, wherein the checkpoint inhibitor is administered prior to administering the PDE1 inhibitor.

2.22 Any preceding method, wherein the checkpoint inhibitor is administered after administering the PDE1 inhibitor.

2.23 Any of the preceding methods, wherein the subject in need thereof was previously or concurrently administered a checkpoint inhibitor therapy.

2.24 Any of the preceding methods, wherein the subject in need thereof is suffering from a disease, disorder or adverse effect of a checkpoint inhibitor therapy.

2.25 The preceding method, wherein the subject is suffering from an inflammatory-related disorder consequent to the checkpoint inhibitor therapy.

2.26 Method 2.24 or 2.25, wherein the subject is suffering from a systemic inflammatory response, a gastrointestinal inflammation-related disorder, an endocrine inflammation-related disorder, a dermatologic inflammation-related disorder, an ophthalmologic inflammation-related disorder, a neurologic inflammation-related disorder, a hematologic inflammation-related disorder, a genitourinary inflammation-related disorder, a respiratory inflammation-related disorder, a musculoskeletal inflammation-related disorder, a cardiac inflammation-related disorder, or a defined systemic inflammation-related disorder.

2.27 Method 2.26, wherein the gastrointestinal inflammation-related disorder is selected from colitis, enterocolitis, colitis complicated by intestinal perforation, hepatitis, and pancreatitis.

2.28 Method 2.26, wherein the endocrine inflammation-related disorder is selected from hypophysitis (e.g., manifested as panhypopitutarism), thyrotoxicosis, hypothyroidism, syndrome of inappropriate secretion of antidiuretic hormone, central adrenal insufficiency, primary adrenal insufficiency, and diabetes mellitus.

2.29 Method 2.26, wherein the dermatologic inflammation-related disorder is selected from a rash, pruritis, vitiligo, dermatitis, sweet syndrome, drug eruption, poliosis, delayed hypersensitivity reaction, alopecia universalis, grover disease, pyoderma gangrenosum, toxic epidermal necrolysis, chronic non-caseation granuloma, bullous pemphigoid, and psoriasis.

2.30 Method 2.26, wherein the ophthalmologic inflammation-related disorder is selected from uveitis, conjunctivitis, orbital inflammation, Grave's ophthalmology, choroidal neovascularization, optic neuropathy, keratitis, and retinopathy.

2.31 Method 2.26, wherein the neurologic inflammation-related disorder is selected from encephalopathy, Guillan-Barre syndrome, polyradiculoneuropathy, symmetrical multifocal neuropathy, transverse myelitis, necrotizing myelopathy, myasthenia gravis, phrenic nerve palsy, immune related meningitis, meningioradiculoneuritis, peripheral neuropathy, autoimmune inner ear disease, multiple sclerosis, and inflammatory enteric neuropathy.

2.32 Method 2.26, wherein the hematologic inflammation-related disorder is selected from thrombocytopenia, pancytopenia, neutropenia, eosinophilia, pure red blood cell aplasia, acquired hemophilia A, and disseminated intravascular coagulopathy.

2.33 Method 2.26, wherein the genitourinary inflammation-related disorder is selected from renal failure, acute/granulomatous interstitial nephritis, acute tubular necrosis, and lymphotic vasculitis (e.g., lymphotic vasculitis of the uterus).

2.34 Method 2.26, wherein the respiratory inflammation-related disorder is selected from pneumonitis and acute respiratory distress.

2.35 Method 2.26, wherein the musculoskeletal inflammation-related disorder is selected from polyarthritis, athralgia, myalgia, chronic granulomatous inflammation of rectus abdominis muscle, and rhabdomyolysis.

2.36 Method 2.26, wherein the cardiac inflammation-related disorder is selected from precarditis and takotsubo like syndrome.

2.37 Method 2.26, wherein the defined systemic inflammation-related disorder is selected from lung sarcoidosis, cutaneous and pulmonary sarcoidosis, polymyalgia rheumatica, giant cell arteritis, muscular sarcoidosis, neurological and pulmonary sarcoidosis, celiac disease, lupus nephritis, dermamyositis, autoimmune inflammatory myopathy, and Vogt-Koyanagi like syndrome.

2.38 Any of the preceding methods, wherein the PDE1 inhibitor and checkpoint inhibitor are administered with radiation therapy or chemotherapy.

2.39 Any of the preceding methods, wherein the PDE1 inhibitor and checkpoint inhibitor are administered concurrently with radiation therapy or chemotherapy.

2.40 Any of the preceding methods, wherein the PDE1 inhibitor and checkpoint inhibitor are administered prior to radiation therapy or chemotherapy.

2.41 Any of the preceding methods, wherein the PDE1 inhibitor and checkpoint inhibitor are administered after radiation therapy or chemotherapy.

2.42 Any of the preceding methods, wherein the PDE1 inhibitor and checkpoint inhibitor are administered together with an additional antitumor agent, chemotherapeutic, gene therapeutic and/or immunologic treatment.

2.43 Any of the preceding methods, wherein the PDE1 inhibitor is a PDE1 inhibitor according to Formulas I, Ia, II, III, IV, V, and/or VI or a compound according to the following:

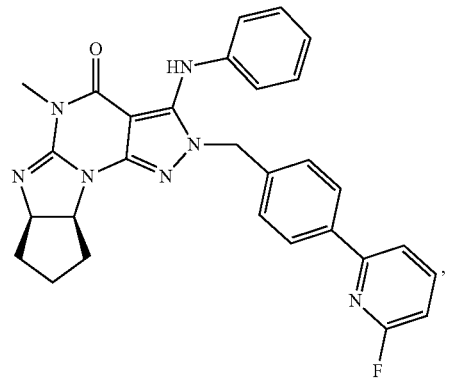

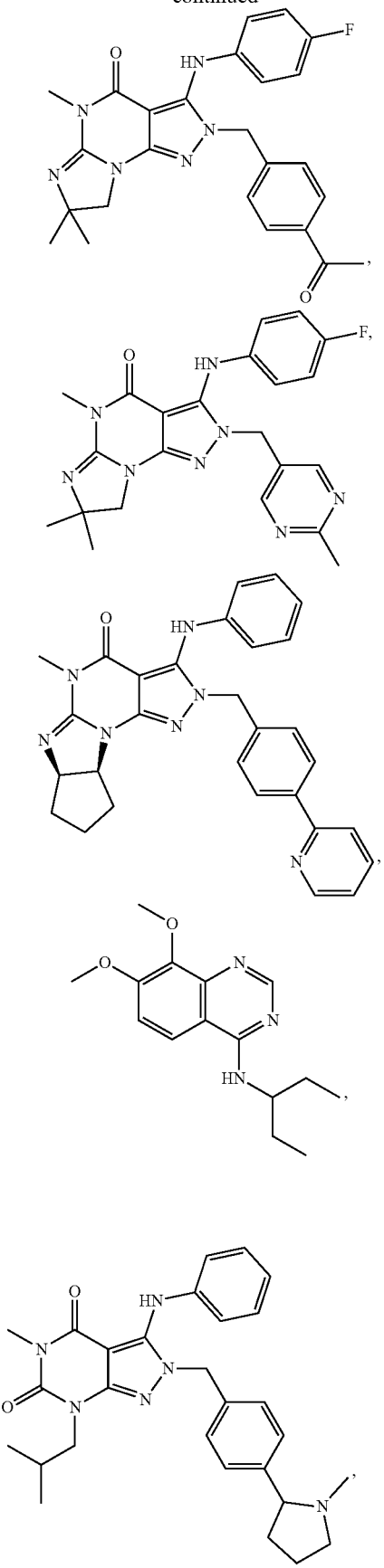
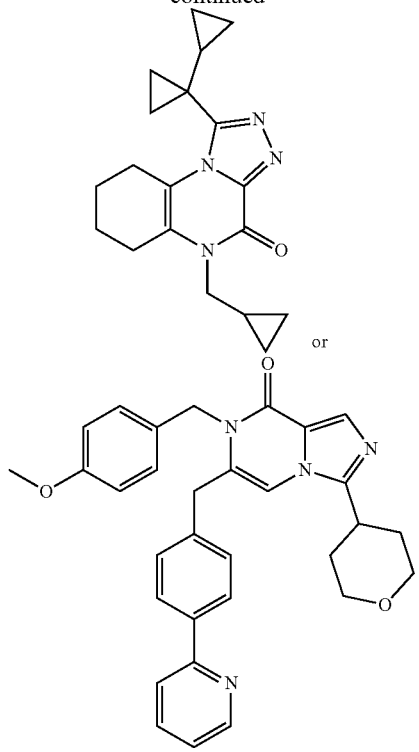
in free or pharmaceutically acceptable salt form.
2.44 Any of the preceding methods, wherein the PDE1 inhibitor is a PDE1 inhibitor according to Formula Ia.
2.45 Any of the preceding methods, wherein the PDE1 inhibitor is a compound as follows:
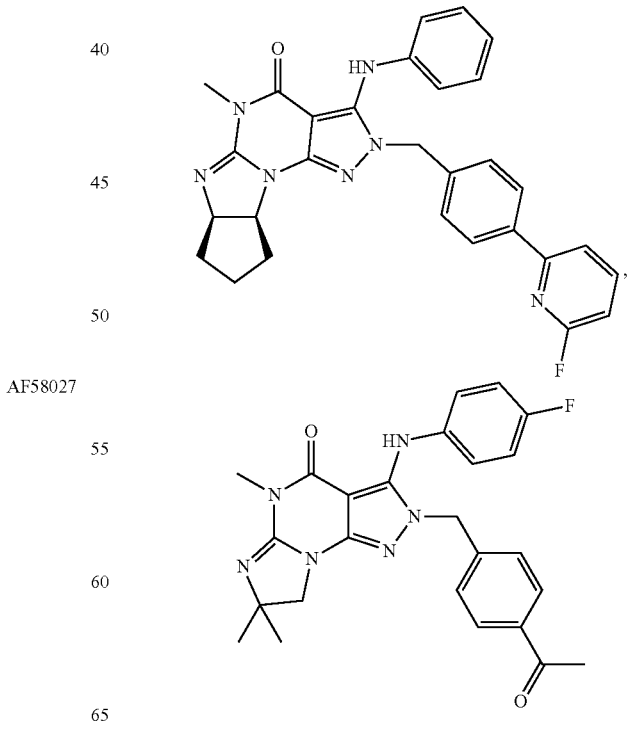
in free or pharmaceutically acceptable salt form.

2.46 Any of the preceding methods, wherein the PDE1 inhibitor is a compound as follows:

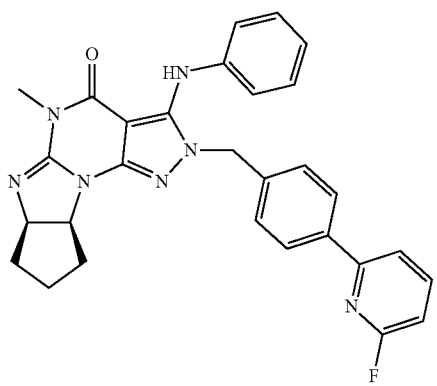 [SMILES: CN1C(=O)c2c(nn(Cc3ccc(-c4cccc(F)n4)cc3)c2Nc2ccccc2)N2C1=N[C@@H]1CCC[C@@H]12]

in pharmaceutically acceptable salt form e.g. monophosphate salt form.

2.47 Any of the preceding methods, further comprising administering a pharmaceutically acceptable amount of a beta blocker to the subject.

2.48 Any of the preceding methods, comprising administration of the PDE1 inhibitor to a patient receiving or scheduled to receive an immunotherapy (e.g. checkpoint inhibitor and/or gene editing or CAR-T therapy).

2.49 The preceding method, wherein the immunotherapy is a CAR-T therapy.

In another embodiment, the disclosure provides a PDE1 inhibitor (e.g., a PDE1 inhibitor according to Formulas I, Ia, II, III, IV, V, and/or VI) for use in prophylaxis or mitigation of a disease, disorder or adverse effect consequent to administration of a checkpoint inhibitor therapy, e.g. for use in any of methods 2, et seq.

In another embodiment, the present application provides for a method (Method 3) of suppressing macrophage or microglial recruitment to metastatic cells comprising administering a pharmaceutically acceptable amount of a PDE1 inhibitor (e.g., a PDE1 inhibitor according to Formulas I, Ia, II, III, IV, V, and/or VI) to a subject in need thereof.

3.1 Method 3, wherein the macrophage or microglial recruitment to metastatic cells is mediated by CCL2.

3.2 Any preceding method, wherein the PDE1 inhibitor is administered in combination with a checkpoint inhibitor as a treatment for a tumor or cancer.

3.3 The preceding method, wherein the tumor or cancer exhibits increased expression of PDE1 in the cancerous or tumorous cells.

3.4 Any of methods 3.2-3.3, wherein the cancerous or tumorous cells exhibit increased expression of PDE1C.

3.5 Any of methods 3.2-3.4, wherein the cancer cells exhibit one or more of increased PDE1 RNA expression, DNA copy number, PDE1 binding (e.g., PET or radio-isotope retention of PDE1 inhibitor molecules), modification to the PDE1 enzyme (i.e., truncation of the receptor leading to loss of calcium/calmodulin control), or PDE1 enzymatic activity (e.g., as measured in an enzymatic assay or as reflected in low levels of cAMP in the cancer cells or subcellular domain, e.g. microtubule domains, of the cancer cells) relative to normal cells of the same tissue type as the cancer cells.

3.6 Any of the preceding methods, wherein the metastatic cells are a tumor or cancer.

3.7 The preceding method, wherein the metastatic cells are a tumor.

3.8 Any of methods 3.6-3.7, wherein the tumor is selected from one or more of acoustic neuroma, astrocytoma, chordoma, CNS lymphoma, craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid, Merkel cell carcinoma, colon carcinoma), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant schwannoma, malignant pheochromocytoma, malignant paraganglioma, melanoma, mercell cell neoplasm, cystosarcoma phylloides, or Wilms tumor.

3.9 Any of methods 3.6-3.8, wherein the tumor or cancer is a glioma, lymphoma, osteosarcoma, melanoma, leukemia, or neuroblastoma.

3.10 Any of methods 3.6-3.9, wherein the tumor or cancer is a glioma (e.g., ependymoma, astrocytoma, oligodendrogliomas, brain stem glioma, optic nerve glioma, or mixed gliomas, e.g., oligoastrocytomas).

3.11 The previous method, wherein the glioma is an astrocytoma (e.g., glioblastoma multiforme).

3.12 Any of methods 3.6-3.11, wherein the tumor or cancer is glioblastoma multiforme or a lymphoma.

3.13 Method 3.6, wherein the condition is a cancer.

3.14 Any of Methods 3.6 or 3.13, wherein the condition is a lung cancer, pancreatic cancer, prostate cancer, a urothelial cancer, cancers of the head and neck, or leukemia.

3.15 Method 3.14, wherein the leukemia is a lymphocytic leukemia or a myelogenous leukemia.

3.16 Method 3.14, wherein the urothelial cancer is a cancer of the kidney, ureter, bladder or urethra.

3.17 Any of methods 3.2-3.16, wherein the checkpoint inhibitor is an inhibitor of CTLA-4, PD-1 and/or PD-L1.

3.18 Any of methods 3.2-3.17, wherein the checkpoint inhibitor comprises one or more members selected from nivolumab, pembrolizumab, cemiplimab, ipilimumab, avelumab, durvalumab, atezolizumab, spartalizumab.

3.19 Any of methods 3.2-3.18, wherein the checkpoint inhibitor is an inhibitor of CTLA-4.

3.20 Any of methods 3.2-3.18, wherein the checkpoint inhibitor is an inhibitor of PD-1.

3.21 Any of methods 3.2-3.18, wherein the checkpoint inhibitor is an inhibitor of PD-L1.

3.22 Any preceding method, wherein the checkpoint inhibitor is administered concurrently with the PDE1 inhibitor.

3.23 Any of methods 3.2-3.22, wherein the checkpoint inhibitor is administered prior to administering the PDE1 inhibitor.

3.24 Any of methods 3.2-3.23, wherein the checkpoint inhibitor is administered after administering the PDE1 inhibitor.

3.25 Any of methods 3.2-3.24, wherein the subject in need thereof was previously or concurrently administered a checkpoint inhibitor therapy.

3.26 Any of methods 3.2-3.25, wherein the subject in need thereof is suffering from a disease, disorder or adverse effect of a checkpoint inhibitor therapy.

3.27 The preceding method, wherein the subject is suffering from an inflammatory-related disorder consequent to the checkpoint inhibitor therapy.

3.28 Method 3.26 or 3.27, wherein the subject is suffering from a systemic inflammatory response, a gastrointestinal inflammation-related disorder, an endocrine inflammation-related disorder, a dermatologic inflammation-related disorder, an ophthalmologic inflammation-related disorder, a neurologic inflammation-related disorder, a hematologic inflammation-related disorder, a genitourinary inflammation-related disorder, a respiratory inflammation-related disorder, a musculoskeletal inflammation-related disorder, a cardiac inflammation-related disorder, or a defined systemic inflammation-related disorder.

3.29 Method 3.28, wherein the gastrointestinal inflammation-related disorder is selected from colitis, enterocolitis, colitis complicated by intestinal perforation, hepatitis, and pancreatitis.

3.30 Method 3.28, wherein the endocrine inflammation-related disorder is selected from hypophysitis (e.g., manifested as panhypopitutarism), thyrotoxicosis, hypothyroidism, syndrome of inappropriate secretion of antidiuretic hormone, central adrenal insufficiency, primary adrenal insufficiency, and diabetes mellitus.

3.31 Method 3.28, wherein the dermatologic inflammation-related disorder is selected from a rash, pruritis, vitiligo, dermatitis, sweet syndrome, drug eruption, poliosis, delayed hypersensitivity reaction, alopecia universalis, grover disease, pyoderma gangrenosum, toxic epidermal necrolysis, chronic non-caseation granuloma, bullous pemphigoid, and psoriasis.

3.32 Method 3.28, wherein the ophthalmologic inflammation-related disorder is selected from uveitis, conjunctivitis, orbital inflammation, Grave's ophthalmology, choroidal neovascularization, optic neuropathy, keratitis, and retinopathy.

3.33 Method 3.28, wherein the neurologic inflammation-related disorder is selected from encephalopathy, Guillan-Barre syndrome, polyradiculoneuropathy, symmetrical multifocal neuropathy, transverse myelitis, necrotizing myelopathy, myasthenia gravis, phrenic nerve palsy, immune related meningitis, meningioradiculoneuritis, peripheral neuropathy, autoimmune inner ear disease, multiple sclerosis, and inflammatory enteric neuropathy.

3.34 Method 3.28, wherein the hematologic inflammation-related disorder is selected from thrombocytopenia, pancytopenia, neutropenia, eosinophilia, pure red blood cell aplasia, acquired hemophilia A, and disseminated intravascular coagulopathy.

3.35 Method 3.28, wherein the genitourinary inflammation-related disorder is selected from renal failure, acute/granulomatous interstitial nephritis, acute tubular necrosis, and lymphotic vasculitis (e.g., lymphotic vasculitis of the uterus).

3.36 Method 3.28, wherein the respiratory inflammation-related disorder is selected from pneumonitis and acute respiratory distress.

3.37 Method 3.28, wherein the musculoskeletal inflammation-related disorder is selected from polyarthritis, athralgia, myalgia, chronic granulomatous inflammation of rectus abdominis muscle, and rhabdomyolysis.

3.38 Method 3.28, wherein the cardiac inflammation-related disorder is selected from precarditis and takotsubo like syndrome.

3.39 Method 3.28, wherein the defined systemic inflammation-related disorder is selected from lung sarcoidosis, cutaneous and pulmonary sarcoidosis, polymyalgia rheumatica, giant cell arteritis, muscular sarcoidosis, neurological and pulmonary sarcoidosis, celiac disease, lupus nephritis, dermamyositis, autoimmune inflammatory myopathy, and Vogt-Koyanagi like syndrome.

3.40 Any of methods 3.2-3.39, wherein the PDE1 inhibitor and checkpoint inhibitor are administered with radiation therapy or chemotherapy.

3.41 Any of methods 3.2-3.40, wherein the PDE1 inhibitor and checkpoint inhibitor are administered concurrently with radiation therapy or chemotherapy.

3.42 Any of methods 3.2-3.41, wherein the PDE1 inhibitor and checkpoint inhibitor are administered prior to radiation therapy or chemotherapy.

3.43 Any of methods 3.2-3.42, wherein the PDE1 inhibitor and checkpoint inhibitor are administered after radiation therapy or chemotherapy.

3.44 Any of methods 3.2-3.43, wherein the PDE1 inhibitor and checkpoint inhibitor are administered together with an additional antitumor agent, chemotherapeutic, gene therapeutic and/or immunologic treatment.

3.45 Any of the preceding methods, wherein the PDE1 inhibitor is a PDE1 inhibitor according to Formulas I, Ia, II, III, IV, V, and/or VI or a compound according to the following:

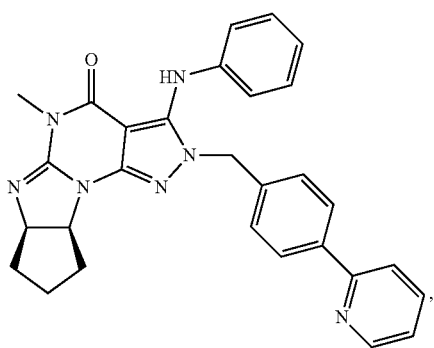
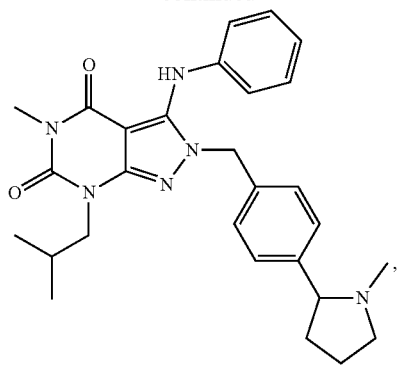
AF58027
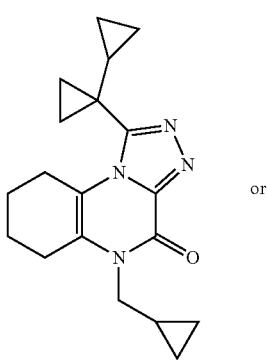
or
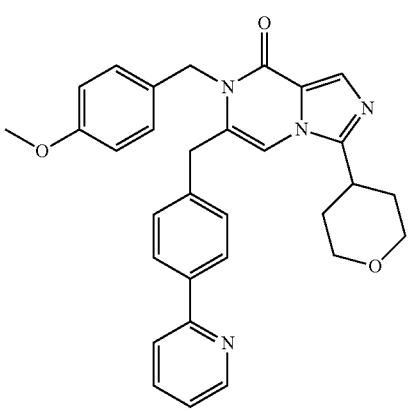
in free or pharmaceutically acceptable salt form.
3.46 Any of the preceding methods, wherein the PDE1 inhibitor is a PDE1 inhibitor according to Formula Ia.

3.47 Any of the preceding methods, wherein the PDE1 inhibitor is a compound as follows:

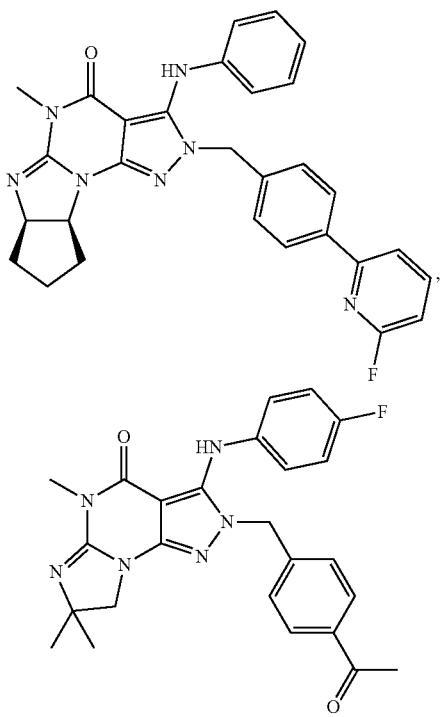

in free or pharmaceutically acceptable salt form.

3.48 Any of the preceding methods, wherein the PDE1 inhibitor is a compound as follows:

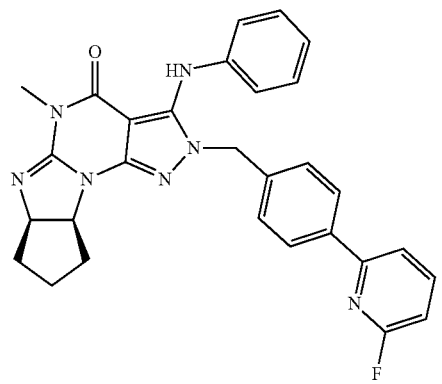 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form, e.g. monophosphate salt form.

3.49 Any of the preceding methods, further comprising administering a pharmaceutically acceptable amount of a beta blocker to the subject.

3.50 Any of the preceding methods, comprising administration of the PDE1 inhibitor to a patient receiving or scheduled to receive an immunotherapy (i.e., CAR-T therapy).

3.51 The preceding method, wherein the immunotherapy is a CAR-T therapy.

Combination Therapies with PDE1 Inhibitors

In another embodiment, the disclosure provides PDE1 inhibitor (e.g., a PDE1 inhibitor according to Formulas I, Ia, II, III, IV, V, and/or VI) use of a suppressing macrophage or microglial recruitment to metastatic cells comprising administering a pharmaceutically acceptable amount of a In some embodiments, the PDE1 inhibitor is administered in combination with other therapeutic modalities. Thus, in addition to the therapies described above, one may also provide to the patient more pharmaceutical therapies in the treatment of a disease or disorder according to the present disclosure. Examples of other therapies include, e.g., checkpoint inhibitors. A particular form of combination therapy will include the use of PDE1 inhibitors.

Combinations may be achieved by administering a single composition or pharmacological formulation that includes the PDE1 inhibitor and one or more additional therapeutic agents, or by administration of two distinct compositions or formulations, separately, simultaneously or sequentially, wherein one composition includes the PDE1 inhibitor and the other includes the additional therapeutic agent or agents. The therapy using a PDE1 inhibitor may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In some embodiments, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a PDE1 inhibitor, or an additional therapeutic agent will be desired. In this regard, various combinations may be employed. By way of illustration, where the PDE1 inhibitor is "A" and the additional therapeutic agent is "B," the following permutations based on 3 and 4 total administrations are exemplary:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Accordingly, in various embodiments, the present disclosure also provides for a pharmaceutical combination [Combination 1] therapy comprising a pharmaceutically effective amount of a PDE1 inhibitor (e.g., a compound according to Formulas I, Ia, II, III, IV, V, and/or VI) and a checkpoint inhibitor, for administration in a method of treating a condition selected from a cancer or tumor, e.g., in accordance with any of Method 1, et seq., or for prophylaxis or mitigation of a disease, disorder or adverse effect consequent to administration of a checkpoint inhibitor therapy, e.g. in accordance with any of Method 2, et seq., or for suppressing macrophage or microglial recruitment to metastatic cells, e.g., in accordance with any of Method 3, et seq. For example, the present disclosure provides for the following Combinations:

1.1 Combination 1 wherein the PDE1 inhibitor and the checkpoint inhibitor are in a single dosage form, e.g., a tablet or capsule, in combination or association with a pharmaceutically acceptable diluent or carrier.

1.2 Combination 1 wherein the PDE1 inhibitor and the checkpoint inhibitor are in a single package, e.g., with instructions for administration simultaneously or sequentially.
1.3 Any of the preceding methods, wherein the PDE1 inhibitor is a PDE1 inhibitor according to Formulas I, Ia, II, III, IV, V, and/or VI or a compound according to the following:
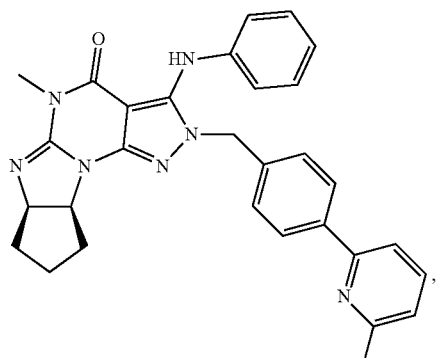
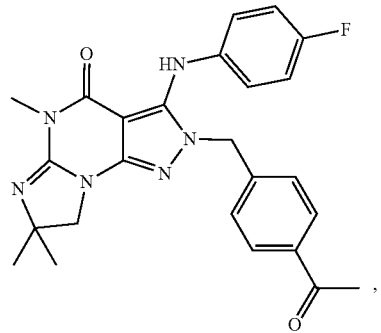
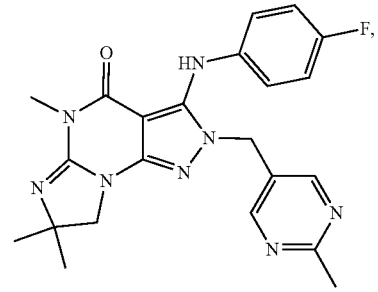
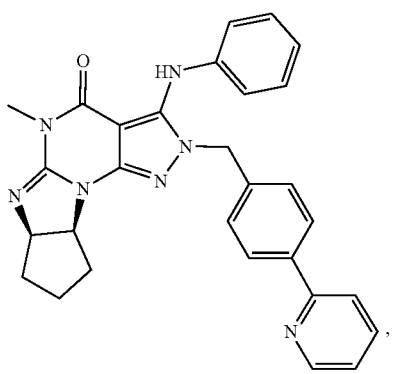
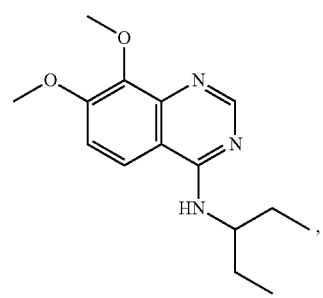
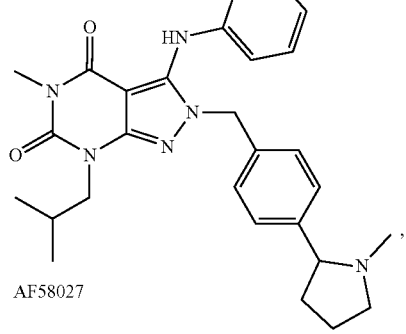
AF58027
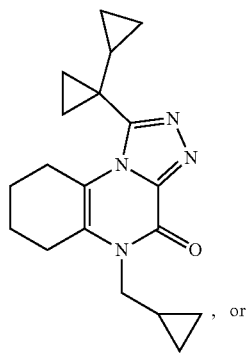
, or -continued

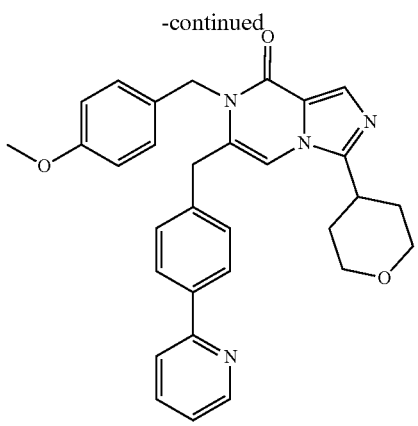

in free or pharmaceutically acceptable salt form.

1.4 Any of the preceding methods, wherein the PDE1 inhibitor is a PDE1 inhibitor according to Formula Ia.

1.5 Any of the preceding methods, wherein the PDE1 inhibitor is a compound as follows:

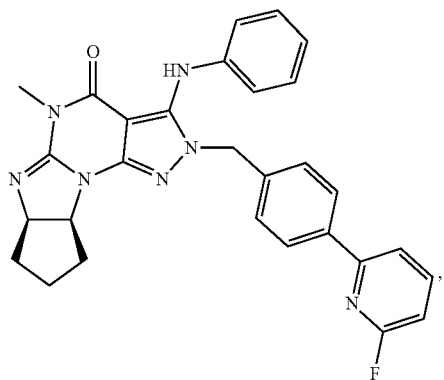

in free or pharmaceutically acceptable salt form.

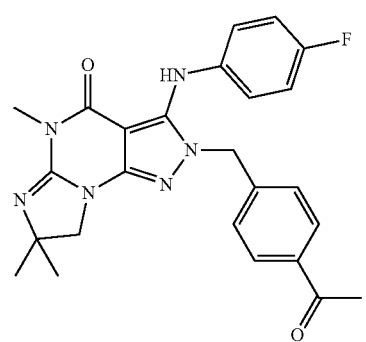

in free or pharmaceutically acceptable salt form.

1.6 Any of the preceding methods wherein the PDE1 inhibitor is a compound as follows:

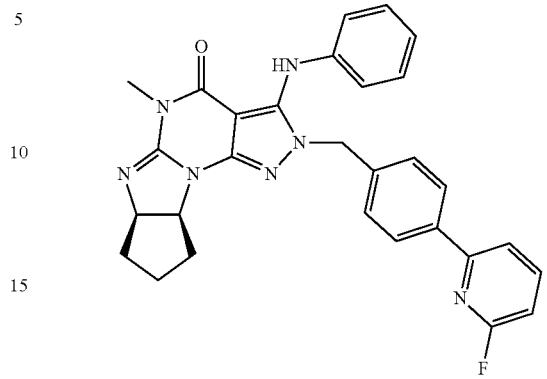

in free or pharmaceutically acceptable salt form.

1.7 Any of the preceding combinations, wherein the checkpoint inhibitor is an inhibitor of CTLA-4.

1.8 Any of the preceding combinations, wherein the checkpoint inhibitor comprises one or more members selected from nivolumab, pembrolizumab, cemiplimab, ipilimumab, avelumab, durvalumab, atezolizumab, spartalizumab.

1.9 Any of the preceding combinations, wherein the checkpoint inhibitor is an inhibitor of CTLA-4.

1.10 Any of combinations 1-1.8, wherein the checkpoint inhibitor is an inhibitor of PD-1.

1.11 Any of combinations 1-1.8, wherein the checkpoint inhibitor is an inhibitor of PD-L1.

1.12 Any of the preceding combinations, wherein the checkpoint inhibitor is administered concurrently with the PDE1 inhibitor.

1.13 Any of the preceding combinations, wherein the checkpoint inhibitor is administered prior to administering the PDE1 inhibitor.

1.14 Any of the preceding combinations, wherein the checkpoint inhibitor is administered after administering the PDE1 inhibitor.

1.15 Any of the preceding combinations, wherein the subject in need thereof was previously or concurrently administered a checkpoint inhibitor therapy.

1.16 Any of the preceding combinations, further comprising a pharmaceutically acceptable amount of a beta blocker.

In some embodiments, the pharmaceutical compositions are administered in combination with one or more antitumor drugs, for example, drugs known to have an effect in treating or eliminating various types of cancers and/or tumors. Non-limiting examples of antitumor drugs are Abemaciclib, Abiraterone Acetate, Abitrexate (Methotrexate), Abraxane (Paclitaxel Albumin-stabilized Nanoparticle Formulation), ABVD, ABVE, ABVE-PC, AC, Acalabrutinib, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin (Chlorambucil), Amifostine, Aminolevulinic Acid, Anastrozole, Aprepitant, Aredia, Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axicabtagene Ciloleucel, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Calquence (Acalabrutinib), Campath (Alemtuzumab), Camptosar (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil-Topical, Flutamide, Folex (Methotrexate), Folex PFS (Methotrexate), Folfiri, Folfiri-Bevacizumab, Folfiri-Cetuximab, Folfirinox, Folfox, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspagase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R—CHOP, R—CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Valrubicin, Valstar (Valrubicin), Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate).

In some embodiments, the PDE1 inhibitor is administered in combination with one or more beta blockers. A non-exhaustive list of such beta blockers includes various beta-adrenergic receptor antagonists, also called beta-blockers, are currently in clinical use for eliminating the harmful chronic myocardial stimulation which is caused by failing heart. Preferred beta-adrenergic receptor antagonists include metoprolol, metoprolol succinate, carvedilol, atenolol, propranolol, acebutolol, acebutolol HCL, betaxolol, betaxolol HCL, nadolol, talinolol, bisoprolol, bisoprolol hemifumarate, carteolol, carteolol HCL, esmolol, esmolol HCL, labetalol, labetalol HCL, metoprolol, metoprolol succinate, metoprolol tartrate, nadolol, penbutolol, penbutolol sulfate, pindolol, propranolol, propranolol HCL, sotalol, sotalol HCL, timolol and timolol hydrogen maleate salt or a pharmaceutically acceptable salt thereof. According to the invention, a beta-adrenergic receptor antagonist may be administered in daily doses, which are clinically accepted for such agents. For example, a suitable daily dose of metoprolol as a tartrate or succinate salt, is about 100-200 mg and for carvedilol about 5-50 mg depending upon the condition to be treated, the route of administration, age, weight and the condition of the patient.

As used herein, the term "antitumor agent" is understood to refer to any chemical agents or drugs effective in preventing or inhibiting the formation or growth of cancers or tumors. Antitumor agents as discussed herein may encompass alkylating agents, antimetabolites, natural products, hormones, and/or antibodies. Treatment of tumors or cancer may include limiting the proliferation, migration and/or invasion of cancerous or tumorous cells in the body, or limiting the symptoms associated with said cancer or tumor. As used herein, antitumor agents are understood to encompass and otherwise be synonymous with anticancer agents.

Methods of Making Compounds of the Disclosure

The PDE1 inhibitors of the Disclosure and their pharmaceutically acceptable salts may be made using the methods as described and exemplified in U.S. Pat. No. 8,273,750, US 2006/0173878, U.S. Pat. No. 8,273,751, US 2010/0273753, U.S. Pat. Nos. 8,697,710, 8,664,207, 8,633,180, 8,536,159, US 2012/0136013, US 2011/0281832, US 2013/0085123, US 2013/0324565, US 2013/0338124, US 2013/0331363, WO 2012/171016, and WO 2013/192556, and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various PDE1 inhibitors and starting materials therefor may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138. All references cited herein are hereby incorporated by reference in their entirety.

The Compounds of the Disclosure include their enantiomers, diastereomers and racemates, as well as their polymorphs, hydrates, solvates and complexes. Some individual compounds within the scope of this disclosure may contain double bonds. Representations of double bonds in this disclosure are meant to include both the E and the Z isomer of the double bond. In addition, some compounds within the scope of this disclosure may contain one or more asymmetric centers. This disclosure includes the use of any of the optically pure stereoisomers as well as any combination of stereoisomers.

It is also intended that the Compounds of the Disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Disclosure may be replaced with deuterium (a stable isotope which is non-radioactive). Examples of known stable isotopes include, but not limited to, deuterium, 13C, 15N, 18O. Alternatively, unstable isotopes, which are radioactive isotopes which contain additional neutrons compared to the abundant nuclides of the same species (i.e., element), e.g., 123I, 131I, 125I, 11C, 18F, may replace the corresponding abundant species of I, C and F. Another example of useful isotope of the compound of the disclosure is the 11C isotope. These radio isotopes are useful for radio-imaging and/or pharmacokinetic studies of the compounds of the disclosure.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

The words "treatment" and "treating" are to be understood accordingly as embracing treatment or amelioration of symptoms of disease as well as treatment of the cause of the disease.

For methods of treatment, the word "effective amount" is intended to encompass a therapeutically effective amount to treat a specific disease or disorder.

The terms "patient" and "subject" include human or non-human (i.e., animal) patient, and are understood to be interchangeable within the context of this disclosure. In particular embodiment, the disclosure encompasses both human and nonhuman. In another embodiment, the disclosure encompasses nonhuman. In other embodiment, the term encompasses human.

The term "comprising" as used in this disclosure is intended to be open-ended and does not exclude additional, un-recited elements or method steps.

Dosages employed in practicing the present disclosure will of course vary depending, e.g. on the particular disease or condition to be treated, the particular Compounds of the Disclosure used, the mode of administration, and the therapy desired. Compounds of the Disclosure may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration of both the PDE1 inhibitor will accordingly be in the range of from about 0.50 to 300 mg, conveniently administered once, or in divided doses 2 to 4 times, daily or in sustained release form. Unit dosage forms for oral administration thus for example may comprise from about 0.2 to 150 or 300 mg, e.g. from about 0.2 or 2.0 to 10, 25, 50, 75 100, 150, or 200 mg of a Compound of the Disclosure, together with a pharmaceutically acceptable diluent or carrier therefor.

Compounds of the Disclosure may be administered by any satisfactory route, including orally, parenterally (intravenously, intramuscular or subcutaneous) or transdermally, but are preferably administered orally. In certain embodiments, the Compounds of the Disclosure, e.g., in depot formulation, is preferably administered parenterally, e.g., by injection.

The Compounds of the Disclosure and the Pharmaceutical Compositions of the Disclosure of the Disclosure may be used in combination with one or more additional therapeutic agents, particularly at lower dosages than when the individual agents are used as a monotherapy so as to enhance the therapeutic activities of the combined agents without causing the undesirable side effects commonly occur in conventional monotherapy. Therefore, the Compounds of the Disclosure may be simultaneously, separately, sequentially, or contemporaneously administered with other agents useful in treating disease. In another example, side effects may be reduced or minimized by administering a Compound of the Disclosure in combination with one or more additional therapeutic agents in free or salt form, wherein the dosages of (i) the second therapeutic agent(s) or (ii) both Compound of the Disclosure and the second therapeutic agent, are lower than if the agent/compound are administered as a monotherapy.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

Pharmaceutical compositions comprising Compounds of the Disclosure may be prepared using conventional diluents or excipients and techniques known in the galenic art. Thus, oral dosage forms may include tablets, capsules, solutions, suspensions and the like.

Example 1

Measurement of PDE1B Inhibition In Vitro Using IMAP Phosphodiesterase Assay Kit

Phosphodiesterase I B (PDEIB) is a calcium/calmodulin dependent phosphodiesterase enzyme that converts cyclic guanosine monophosphate (cGMP) to 5'-guanosine monophosphate (5'-GMP). PDEIB can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, CA) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Amp). Inhibition of phosphodiesterase, therefore, is detected as a decrease in Amp.

Enzyme Assay

Materials: All chemicals are available from Sigma-Aldrich (St. Louis, MO) except for IMAP reagents (reaction buffer, binding buffer, FL-GMP and IMAP beads), which are available from Molecular Devices (Sunnyvale, CA).

Assay: The following phosphodiesterase enzymes may be used: 3',5'-cyclic-nucleotide-specific bovine brain phosphodiesterase (Sigma, St. Louis, MO) (predominantly PDEIB) and recombinant full length human PDE1A and PDE1B (r-hPDE1A and r-hPDE1B respectively) which may be produced e.g., in HEK or SF9 cells by one skilled in the art. The PDE1 enzyme is reconstituted with 50% glycerol to 2.5 U/ml. One unit of enzyme will hydrolyze 1.0 μM of 3',5'-cAMP to 5'-AMP per min at pH 7.5 at 30° C. One part enzyme is added to 1999 parts reaction buffer (30 μM CaCl 2, 10 U/ml of calmodulin (Sigma P2277), 10 mM Tris-HCl pH 7.2, 10 mM MgCl 2, 0.1% BSA, 0.05% NaN3) to yield a final concentration of 1.25 mU/ml. 99 μl of diluted enzyme solution is added into each well in a flat bottom 96-well polystyrene plate to which 1 μL of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μL of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, CT) to measure the fluorescence polarization (Amp).

A decrease in GMP concentration, measured as decreased Amp, is indicative of inhibition of PDE activity. IC50 values are determined by measuring enzyme activity in the presence of 8 to 16 concentrations of compound ranging from 0.0037 nM to 80,000 nM and then plotting drug concentration versus AMP, which allows IC50 values to be estimated using nonlinear regression software (XLFit; IDBS, Cambridge, MA).

The Compounds of the Invention are tested in an assay as described or similarly described herein for PDE1 inhibitory activity. For example, Compound 214, is identified as a specific PDE1 inhibitor of formula:

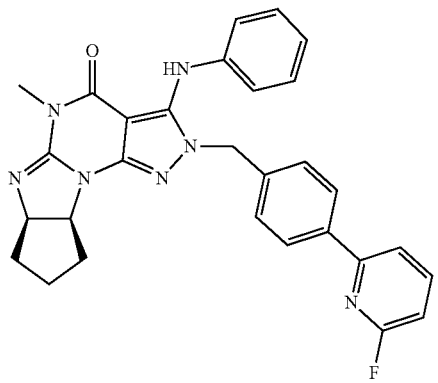 [SMILES: CN1C(=O)c2c(nn(Cc3ccc(-c4cccc(F)n4)cc3)c2Nc2ccccc2)N2C1=N[C@@H]1CCC[C@@H]12]

This compound has efficacy at sub-nanomolar levels vs PDE1 (IC$_{50}$ of 0.058 nM for bovine brain PDE1 in the assay described above) and high selectivity over other PDE families, as depicted on the following table:

| PDE Target | IC50 (nM) | ratio PDEx/PDE1 |
| --- | --- | --- |
| bovine brain PDE1 | 0.058 | 1 |
| hPDE2A | 3661 | 63121 |
| hPDE3B | 3120 | 53793 |
| hPDE4A | 158 | 2724 |
| r-bovine PDE5A | 632 | 10897 |
| bovine retina PDE6 | 324 | 5586 |
| hPDE7B | 355 | 6121 |
| hPDE8A | 3001 | 51741 |
| hPDE9A | 16569 | 285672 |
| hPDE10A | 1824 | 31448 |
| hPDE11A | 1313 | 22638 |

The compound is also highly selective versus a panel of 63 receptors, enzymes, and ion channels. These data, and data for other PDE1 inhibitors described herein, are described in Li et al., J. Med. Chem. 2016: 59, 1149-1164, the contents of which are incorporated herein by reference.

Example 2

Inhibition of Monocyte to Activated Macrophage Transition and Interaction with ANP PDE1 is induced in the inflammatory monocyte-to-activated-macrophage transition mediated by GM-CSF, and this transition can be inhibited by PDE1 knockdown. Bender and Beavo, 2006 PNAS 103, 460-5. Atrial natriuretic peptide (ANP) elevates cGMP levels, by activating the ANP catalytic receptor, which stimulates intracellular guanylyl cyclase activity to convert GTP to cGMP. ANP has an anti-inflammatory effect on macrophages, reducing the secretion of inflammatory mediators in macrophages. Kiemer, et al., Ann Rheum Dis. 2001 November; 60(Suppl 3): iii68-iii70. Specifically, ANP inhibits the lipopolysaccharide (LPS)-induced expression of inducible nitric oxide synthase (iNOS) in macrophages, reduces the activation of NF-κB, inhibits the macrophage release of TNFα and interleukin 1β (IL1β), but not secretion of the anti-inflammatory cytokines IL10 and IL1 receptor antagonist (IL1ra).

We have shown that there is a synergistic effect between ANP and PDE1 inhibition. An immortalized human promyeloid cell line (HL60 from ATCC) is grown, differentiated and harvested as described in Bender, A T, and Beavo, J A, 2006, *PNAS* 103, 460-465. The cells are grown in HEPES buffered RPMI 1640 medium with penicillin, streptomycin, and 10% fetal bovine serum. Phorbol-12-myristate-13-acetate (PMA), at 100 nM for 3 days, is used to differentiate the HL60 cells into macrophage-like cells. Following differentiation, the cells are incubated with a PDE1 inhibitor or vehicle (DMSO) beginning at time 0. At 40 minutes, 5 μM ionomycin (a calcium ionophore) is added. At 50 minutes, 100 nM ANP was added. At 60 minutes, the cells are harvested. Total cGMP levels are measured using a competitive ELISA (Bender and Beavo, 2006).

A representative PDE1 inhibitor, (6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-one, disclosed as Example 20 of U.S. Pat. No. 8,273,750, having the following structure:

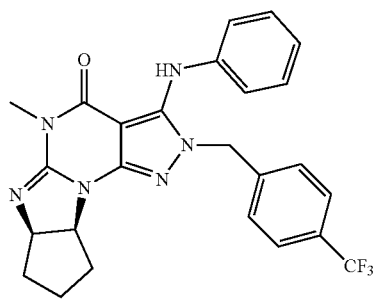 [SMILES: CN1C(=O)c2c(nn(Cc3ccc(C(F)(F)F)cc3)c2Nc2ccccc2)N2C1=N[C@@H]1CCC[C@@H]12]

is tested for its effect on cGMP levels in this system. Like Compound 214, this compound is a potent and selective inhibitor of PDE1 (Ki=0.68 nM bovine brain PDE1 assay described above). The cGMP level induced in the HL60 cells by treatment with 100 nM ANP in combination with 100 nM of the PDE1 inhibitor is greater than that induced by either the ANP alone or the PDE1 inhibitor alone. In addition, the cGMP level attained by co-treatment with ANP and the PDE1 inhibitor is much greater than that obtained by co-treatment with ANP and a mixed PDE1/PDE5 inhibitor, SCH 51866 (used at 5 μM). In this experiment, the calcium ionophore ionomycin (used at 5 μM) is used to raise the intracellular calcium level and to counteract the cGMP rise induced by ANP. The decreasing cGMP signal caused by the activation of PDE1 by ionomycin is synergistically prevented by the combination of a PDE1 inhibitor and sub-optimal levels of ANP. Addition of ionomycin has only a weak cGMP lowering effect when combined with ANP and the PDE1 inhibitor.

Example 3

Effect of PDE1 Inhibitors on Microglia-Derived Cells

Neuroinflammatory processes are regulated largely by microglia. Microglia have activation states somewhat similar to macrophages and in response to IFN-γ or lipopolysaccharide (LPS), they will be activated to release pro-inflammatory cytokines such as TNF-, IL-1β, and reactive oxygen species/reactive nitrogen species (ROS/NOS). Under other circumstances, they can be activated to release anti-inflammatory cytokines, such as IL-10, and to participate in tissue repair. The immortalized murine microglial cell line BV-2 is used as a model for microglia signaling. Stansley et al. Journal of Neuroinflammation 2012, 9:115.

BV2 cells are treated with lipopolysaccharide (LPS) and the level of PDE expression is measured using RNAseq analysis. The data are presented in FIG. 1. "FPKM" represents the "Fragment Reads per kilobase of exon per million reads mapped". After treatment with LPS, an endotoxin associated with the inflammatory response, levels of PDE1B, show relatively large increases in RNA expression when compared to other members of the PDE family of enzymes. PDE1B is among the phosphodiesterase subfamilies to show large increases in RNA expression upon LPS administration.

BV2 cells are further assessed by RNAseq analysis with LPS stimulation in the presence or absence of rolipram (a specific PDE4 inhibitor), and in the presence or absence of Compound 214, which is a specific PDE1 inhibitor of formula:

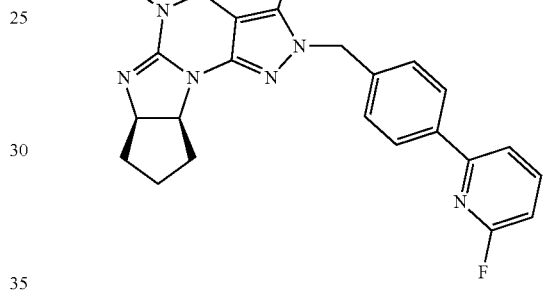

209 mRNA transcripts are decreased in the presence of LPS+rolipram vs. LPS alone; 138 transcripts are decreased in the presence of Compound 214+LPS vs. LPS alone. The overlap between the two sets is 48 transcripts. Similarly 156 transcripts are elevated in the presence of LPS+rolipram vs. LPS alone; 149 transcripts are elevated in the presence of Compound 214+LPS vs. LPS alone. The overlap between the two sets is 45 transcripts.

In a further experiment, an analysis of expression in in LPS-stimulated BV2 cells in the presence and absence of Compound 214 and Rolipram, shows that the differentially expressed genes for each pair ((LPS vs LPS+rolipram, LPS vs LPS+ITI-214) share about half of the most highly significant genes. For example, the assay demonstrates 1240 genes significantly affected by Compound 214 but not Rolipram, 1463 significantly affected by Rolipram but not Compound 214, and only 683 affected by both, an overlap of only about half.

The relatively small overlaps indicate that the effects of PDE1 inhibitors on these cells in response to LPS stimulation are very different from the effects of PDE4 inhibitors. While PDE4 inhibitors are often considered to be anti-inflammatory, the two types of inhibitors in this case are, for the most part, affecting expression of completely different genes.

Moreover, the expression levels of PDEs in BV2 cells to that of mouse brain microglia as determined by RNAseq quantitation of gene transcripts are compared. As detailed in Table A, PDE1B is the second most abundant PDE transcript in freshly isolated mouse microglia, and the most abundant PDE transcript in BV2 cells. PDE4B, PDE4A, PDE7A, and PDE8a expression is also substantial (≥0.7 FPKM/RPKM) in both cell types. Among the several PDEs enzymes detected by RNA-Seq in the BV2 cells, PDE1 is the only one with the ability to hydrolyze both cAMP and cGMP. The relative abundance of PDE1B and PDE4 isoenzymes in BV2 cells potentially indicate to that these are an adequate model for inhibitor studies (Table A):

TABLE A

| Expression retained | | | | | |
|---|---|---|---|---|---|
| | Pde1b | Pde4b | Pde4a | Pde7a | Pde8a |
| Microglia | 9.9 | 8.1 | 2.3 | 1.8 | 0.4 |
| BV2 cells | 4.2 | 1.5 | 2.8 | 0.7 | 0.4 |

| Abundant, expression lost | | | | |
|---|---|---|---|---|
| | Pde3b | Pde2a | Pde8b | Pde9a |
| Microglia | 33.6 | 9.6 | 2 | 0.5 |
| BV2 cells | X | 0.2 | X | X |

| Other, expression lost | | | | |
|---|---|---|---|---|
| | Pda4d | Pde1a | Pde10a | Pda7b |
| Microglia | 0.4 | 0.3 | 0.3 | 0.3 |
| BV2 cells | X | X | X | X |

| Not In microglia | | | |
|---|---|---|---|
| | Pde1c | Pde4c | Pde11a |
| Microglia | X | X | X |
| BV2 cells | X | 1.2 | X |

X = FPKM or APKM ≤0.1

Example 4

Effect on IL1β Expression in Microglia-Derived Cells

Figure 2:
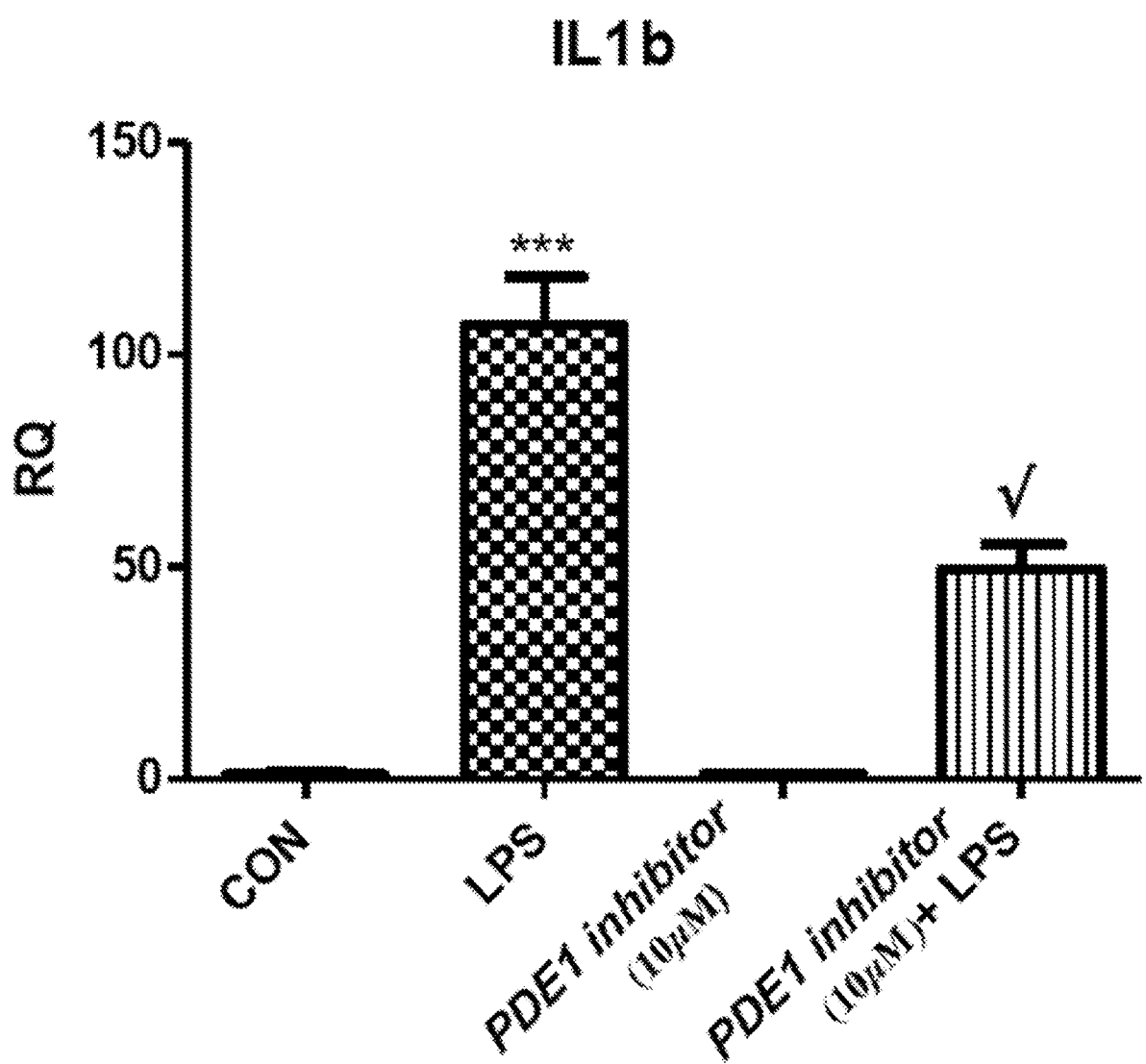
FIG. 2 depicts that a PDE1 inhibitor (Compound 214) suppresses LPS-induced IL1β in BV2 cells

BV2 cells are incubated with (i) LPS (10 microgram/ml), (ii) Compound 214 (10 microgram/ml), or (iii) LPS and Compound 214. Levels of IL1 are measured using quantitative PCR of IL1β mRNA. IL1β is considered a marker of inflammation. Results are depicted in FIG. 2 (RQ: relative quantification of changes in gene expression in treated versus control samples; ***$p<0.01$ vs control, √$p<0.01$ vs LPS alone; ANOVA with Newman-Keuls post-hoc test). Administration of a PDE1 inhibitor of the present invention thus significantly blunts the LPS-induced increase in expression of IL1β in microglia-derived cells.

Example 5—Effect on Neuroinflammatory Gene Expression in BV2 Cells

Figure 3A:
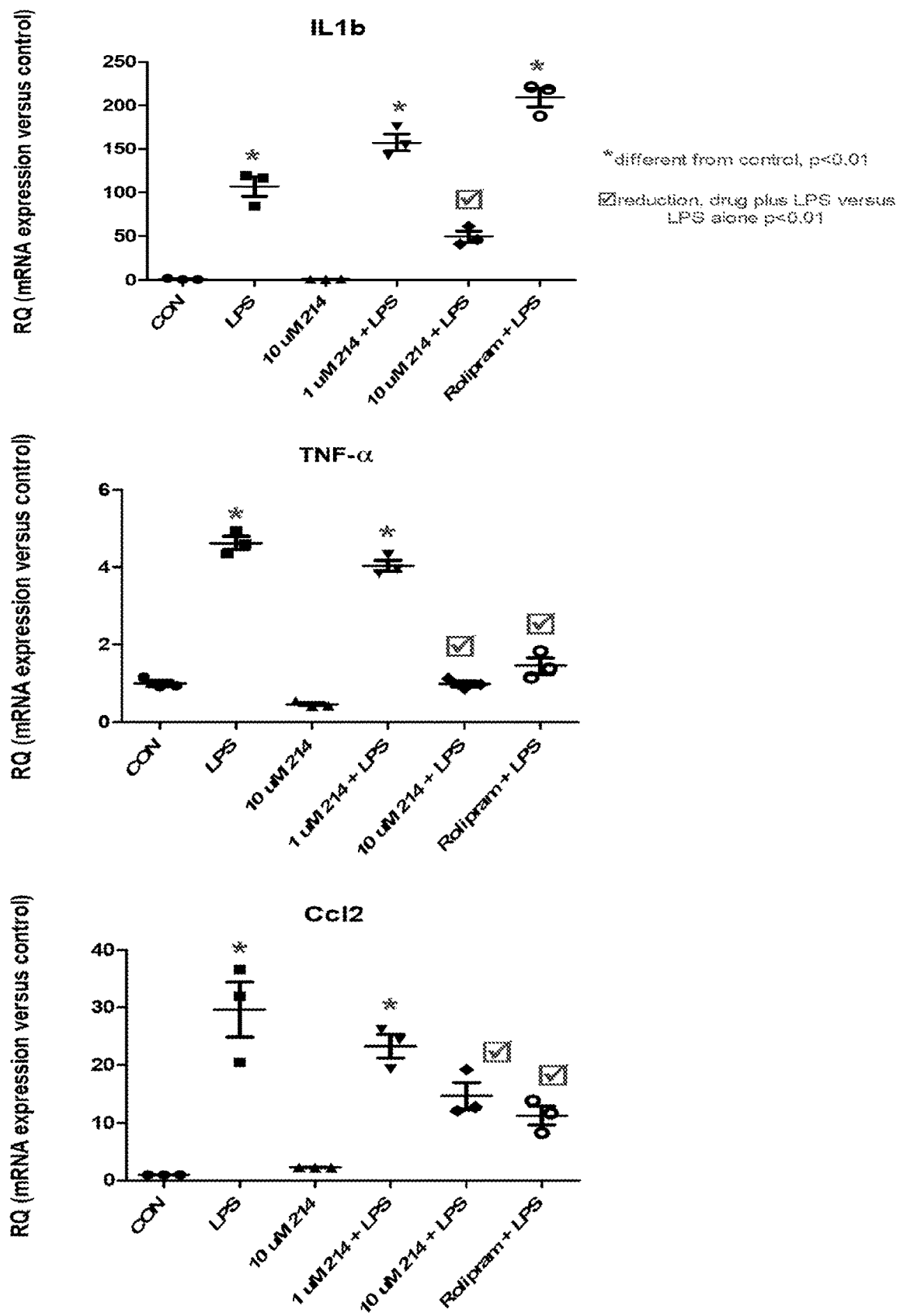
FIG. 3a depicts that a PDE1 inhibitor (Compound 214) significantly reduces the LPS-induced increase in expression of the inflammatory cytokines IL1β, TNF-α, and Ccl2 in BV2 cells, as measured by quantitative PCR, while a PDE4 inhibitor, rolipram, displays a different profile. In a separate experiment, FIG. 3b demonstrates that administration of a PDE1 inhibitor of the present invention (Compound 214) greatly reduces or blunts LPS-induced changes in proinflammatory markers in BV2 cells (FIG. 3b).

Administration of a PDE1 inhibitor of the present invention (Compound 214) at 10 μM significantly reduces the LPS-induced increase in expression of the inflammatory cytokines IL1β, TNFα, and Ccl2 in BV2 cells, as measured by quantitative PCR, as described in Example 4 with respect to IL1β. The PDE4 inhibitor, rolipram, displays a different profile, increasing IL1β expression, while reducing expression of TNF-α and Ccl2. Data are presented in FIG. 3a.

Figure 3B:
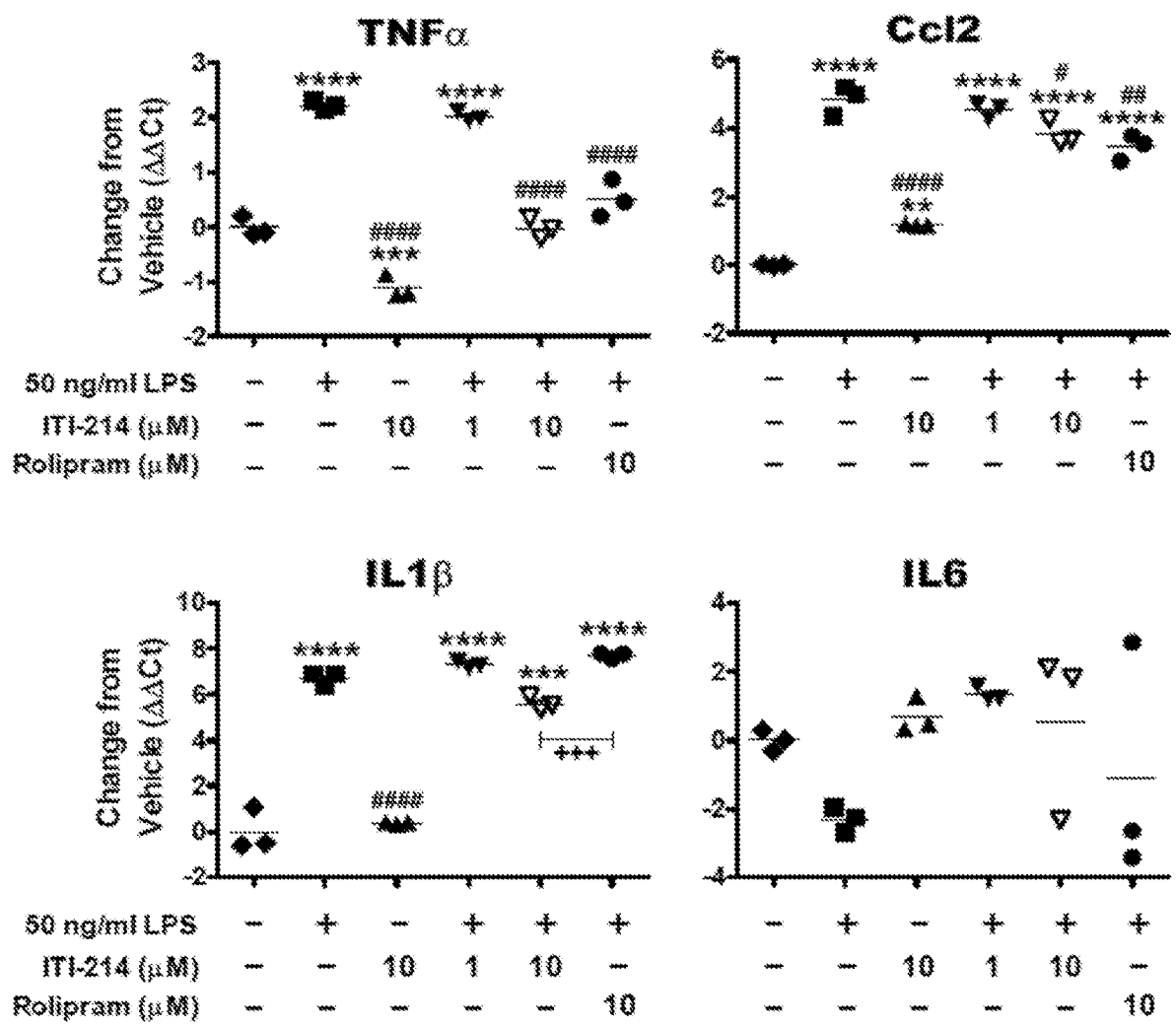

In a separate experiment, administration of a PDE1 inhibitor of the present invention (Compound 214) greatly reduces or blunts LPS-induced changes in proinflammatory markers in BV2 cells (FIG. 3b). BV2 cells are pretreated with compound, ITI-214 or rolipram, a PDE4 inhibitor, then stimulated with 50 ng/ml LPS for 4 hours. Expression levels of TNF, IL1β, Ccl2, and IL6 are measured. Normalized mRNA levels are shown as change from vehicle (ΔΔCt) and compared using a one-way ANOVA. Lines denote the mean. * Significantly different from vehicle, #Significantly different from LPS. * $p<0.05$, $p<0.01$, *$p<0.001$, ****$p<0.0001$. The mRNA transcripts for TNF, IL1β, and Ccl2—three of the four cytokines studied in vivo—were elevated in BV2 cells treated with 50 ng/ml LPS. The mRNA signals for TNF and Ccl2 were significantly decreased by treatment with ITI-214 (10 μM), and IL1β mRNA signal trended downward.

Example 6—Inhibition of LPS-Induced TNFα Release from BV2 Cells

PDE1 inhibition reduces LPS-induced TNFα gene expression and release from BV2 cells.

Figure 4:
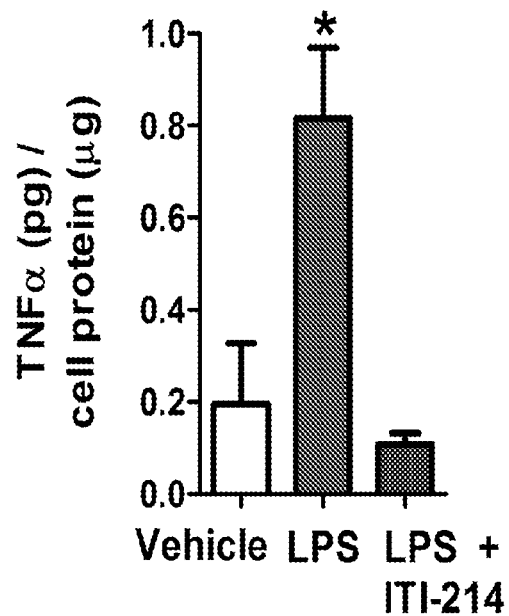
FIG. 4 depicts inhibition of LPS-induced TNFα release from BV2 cells.
Figure 4:
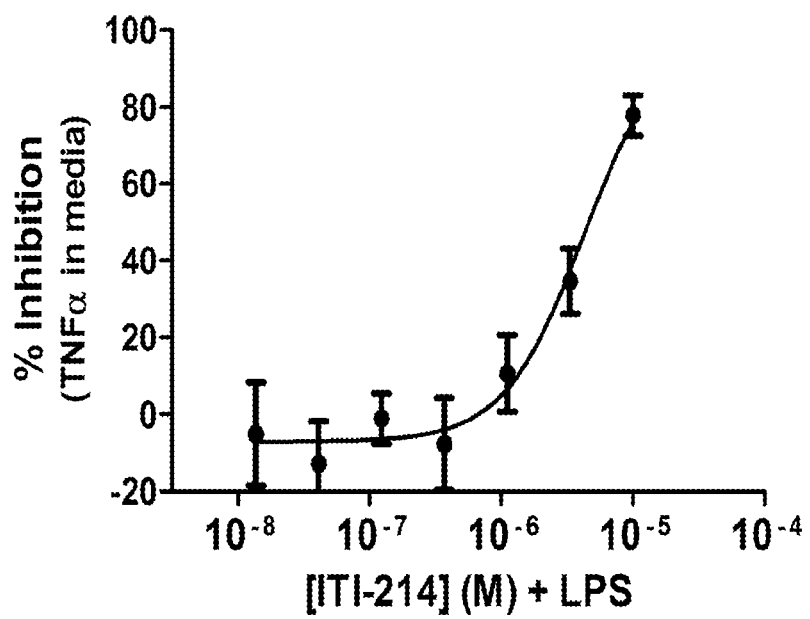

TNFα release: TNFα levels are measured in BV2 conditioned media and normalized to cell protein levels. Inhibition of LPS-induced TNFα release from BV2 cells is depicted in FIG. 4. The left panel shows BV2 cells treated with 10 μM Compound 214 and 50 ng/ml LPS (one-way ANOVA, *$p<0.05$, Vehicle n=16, LPS n=31, LPS+214 n=14). The right panel shows a dose-dependent inhibition of LPS-induced TNFα release (50 ng/ml LPS stimulation) in response to Compound 214 (measured as % inhibition of total LPS response per experiment).

Figure 5:
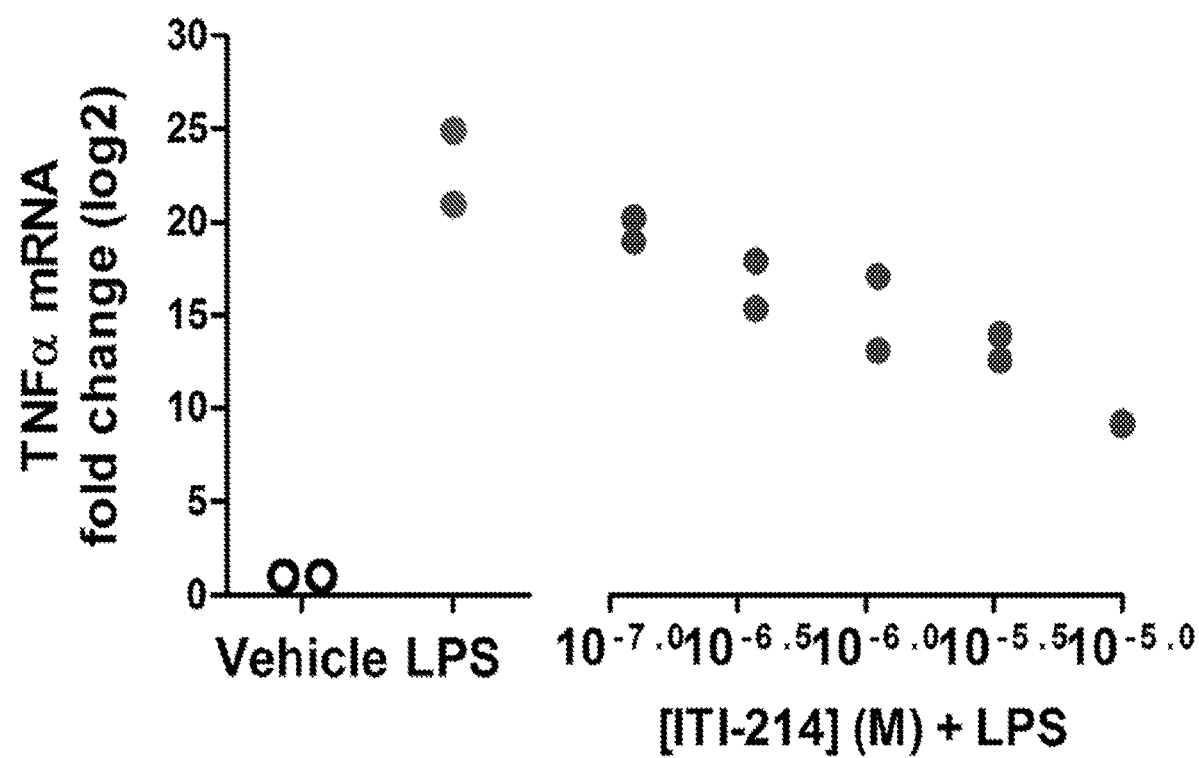
FIG. 5 depicts dose dependent reduction by a PDE1 inhibitor of LPS-stimulated TNFα mRNA expression.

TNFα Gene Expression:

FIG. 5 shows that this dose dependent reduction of TNFα release as measured in the media corresponds to a reduction in TNFα mRNA expression.

Example 7—Effect on Neuroinflammatory Gene Expression in BV2 Cells and to In Vivo Mouse Striatum The effects of a selective PDE1 inhibitor (Compound 214) are tested in LPS stimulated BV2 cells by measuring changes in cytokine release using ELISA and in gene expression using RT-qPCR and RNA-Seq. (Experiment A (n=4): (1) Vehicle; (2) 10 μM Compound 214; (3) 50 ng/ml LPS; (4) 50 ng/ml LPS+10 μM Compound 214; Experiment B (n=2): (1) 50 ng/ml LPS; (2) 50 ng/ml LPS+10 μM Compound 214; (3) 50 ng/ml LPS+10 μM Rolipram (a known potent PDE4 inhibitor)). The test compound is added first, the LPS is added one hour later, and the cells and/or media are harvested at five hours from commencement of the experiment.

PDE1 inhibition prevents LPS-induced increases in TNFα release in BV2 cells. Similarly, LPS-induced increases in TNFα, IL-1β, and Ccl2 mRNA expression are reduced by >50% both in BV2 cells and in mice ($p<0.01$) upon PDE1 inhibition. To better understand the actions of PDE1 inhibition on resting and LPS-activated microglia, we examine transcriptional regulation using RNA-Seq. A subset of genes whose transcript expression is significantly changed with PDE1 inhibition is identified. Using gene ontology software (AmiGO 2), it is seen that these genes are significantly ($p<0.05$) enriched in cell migration and extravasation pathways as well as inflammatory pathways. Of the genes induced by LPS, a subset is attenuated by PDE1 inhibition, all of which are significantly associated with inflammatory pathways ($p<0.05$). PDE4 inhibition attenuates a different subset of LPS-induced genes, demonstrating the unique properties of our target (about 17% overlap with PDE1 inhibition).

Cells: BV2 mouse microglial cell line (ICLC, Italy) grown in 2% or 10% heat-inactivated FBS.

TNFα ELISA: Thermo Fisher mouse TNFα colorimetric, sandwich ELISA kit. Interpolate values from standard curve. Dose response is fit to a 4-parameter logistic curve.

RTqPCR: RNA from BV2 cells purified using RNeasyKit (Qiagen) and from mouse tissue using TRIzol (Ambion). TaqMan primer-probe assays from Thermo Fisher. mRNA levels for all conditions are normalized to GAPDH and to vehicle control (ΔΔCt). Data are analyzed statistically using one-way ANOVA with the Bonferroni post-test for multiple comparisons.

Our results indicate that inhibition of PDE1 regulates activity in microglia, reducing expression of inflammatory genes, providing a rationale to use PDE1 inhibitors to treat toxic neuroinflammation.

RNASeq: Flashfreeze BV2 cells, isolate RNA, prepare a library using polyA selection, and conduct 1×50 bp single read sequencing on the Illumina HiSeq 2500 in High Output mode (using V4 chemistry). Genes are mapped to reference genome (GRCm38) using CLC Genomics Server. Number of reads per sample average ~17 million. Differential gene expression analysis is performed using DESeq2software (Bioconductor.org). Differentially expressed genes (p<0.01, Waldtest) are reported as log 2(fold change).

The following table demonstrates a summary of initial results of neuroinflammatory biomarker expression in both BV2 cells and mouse striatum subject to LPS administration in the presence or absence of a PDE1 inhibitor (Compound 214) or a PDE4 inhibitor (rolipram). The results are based upon an evaluation of samples using Q-PCR.

the expression of TNF and Ccl2. In this experiment, levels of IL1-beta and IL6 trended to lower levels as well, but do not reach significance.

Example 8—Effect on BV2 Chemotaxis

Dying neurons lose membrane integrity and release ATP which is quickly hydrolyzed to ADP, a chemotaxis signal to microglia to migrate to the site of injury where they phagocytose cellular debris. The target on microglia and on BV2 cells, a microglia cell line, for ADP chemotaxis is the $G_{i/o}$ coupled purinergic receptor, P2Y12. This G-protein typically inhibits adenylyl cyclase and thus the formation of cAMP, yet increased cAMP has been documented with activation of P2RY12 by ADP in this system. When the cAMP levels are enhanced beyond the level triggered by ADP, for example by addition of forskolin, chemotaxis toward ADP is inhibited. In this system, cAMP phosphorylates the focal adhesion associated protein, vasodilator stimulated phosphoprotein (VASP), through activation of protein kinase A (PKA), and prolonged phosphorylation by augmented cAMP or inhibition of PP2A is inhibitory to migration.

A first test was carried out to test Compound 214's (shown above in Example 1) ability to inhibit chemotaxis of BV2 cells. Chemotaxis towards 100 μM ADP was measured in a Boyden chamber system for 4 hrs against a vehicle control. BV2 cells were added to the upper chamber of a 5 μm pore Boyden chamber with 100 μM ADP or vehicle in the lower chamber and incubated at 37'C with 5% $CO_2$ for 4 hours. The curve was fit to a 4-parameter logarithmic equation with

| Biomarker | BV2 + LPS | PDE1 Inhibitor | rolipram | Striatum Mouse + LPS | PDE1 Inhibitor | rolipram |
|---|---|---|---|---|---|---|
| Tumor necrosis factor | UP | Down | Down | UP | NC | Down |
| Interleukin 1 beta | Up | Down | UP UP | UP | NC | UP-UP |
| Interleukin 6 | NC | NC | NC | NC | NC | UP-UP |
| Chemokine (C—C) motif Ligand 2 | UP | Down | Down | UP | Down | Down |
| Leukemia inhibitory factor | NC | NC | UP | NC | NC | NC |
| Oncostatin M | NO | UP | UP | UP | Down | Down |

Administering a PDE1 inhibitor of the present invention correlates with either a decrease or no change in the expression of biomarkers: IL1β, TNF-α, and Ccl2 compared to samples treated only with LPS. Interestingly, the anti-inflammatory profile of the PDE1 inhibitor is quite different from that of the PDE4 inhibitor.

Figure 6:
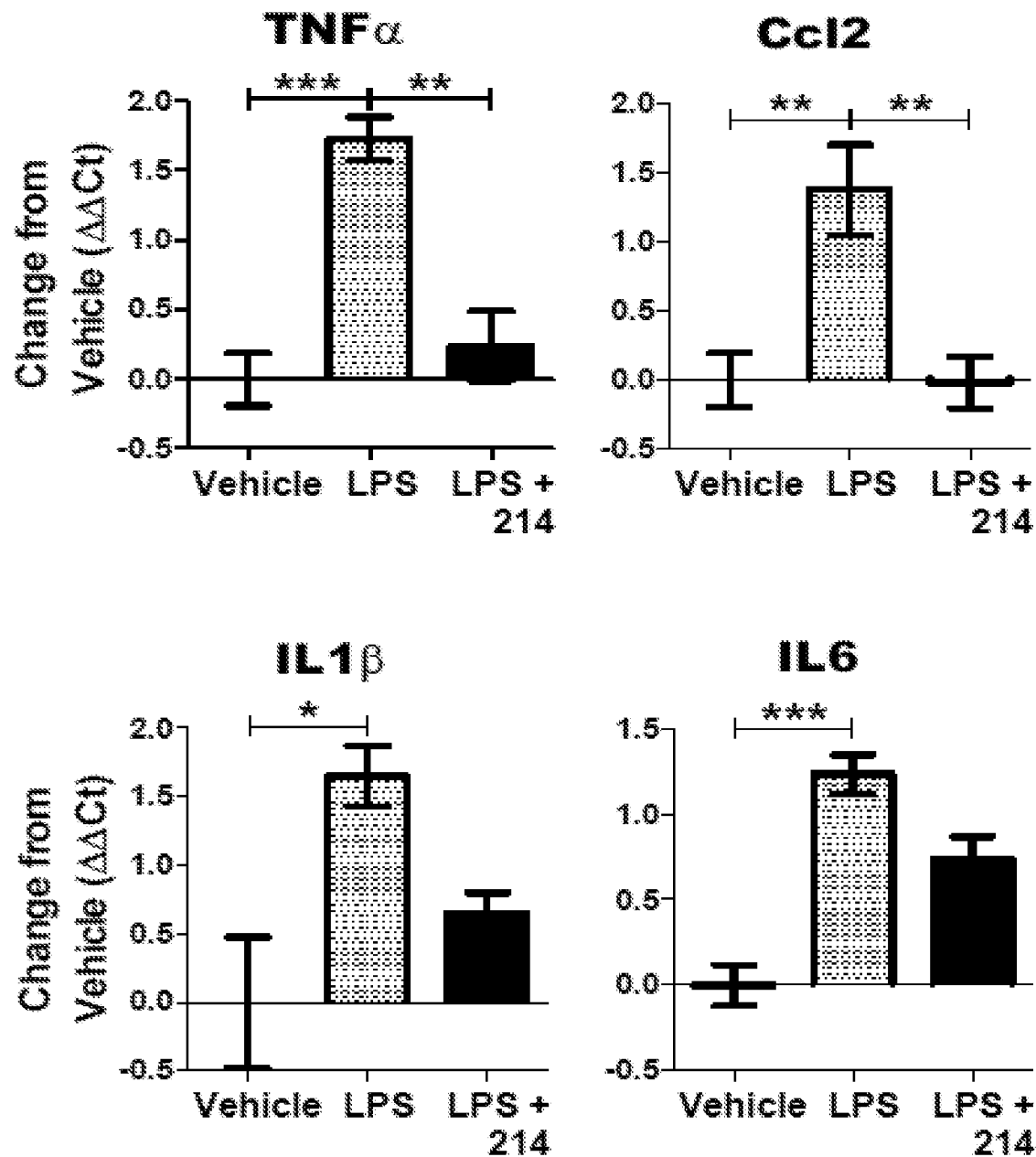
FIG. 6 depicts a PDE1 inhibitor (Compound 214) prevents LPS-induced inflammatory gene expression changes in mice. Adult mice are treated with vehicle (white bars), 500 μg/kg LPS s.c. (gray bars), or 10 mg/kg ITI-214 i.p. and 500 μg/kg LPS s.c. (black bars) for 2 hours (n=4). Striatal tissue is analyzed for mRNA levels of TNF, IL1□, Ccl2, and IL6. Expression levels are shown as change in Q-PCR signal from vehicle (□□Ct) and compared using an ANOVA. * $p<0.05$,  $p<0.01$, * $p<0.001$.

Data from yet another experiment measuring the effect of PDE1 inhibition on inflammatory gene expression in mouse striatum is depicted in FIG. 6. Adult mice are treated with vehicle (white bars), 500 μg/kg LPS s.c. (gray bars), or 10 mg/kg (Compound 214) i.p. and 500 μg/kg LPS s.c. (black bars) for 2 hours (n=4). Striatal tissue is analyzed for mRNA levels of TNF, IL1β, Ccl2, and IL6. Expression levels are shown as change in Q-PCR signal from vehicle (ΔΔCt) and compared using an ANOVA. * p<0.05, p<0.01, *p<0.001.

Figure 7:
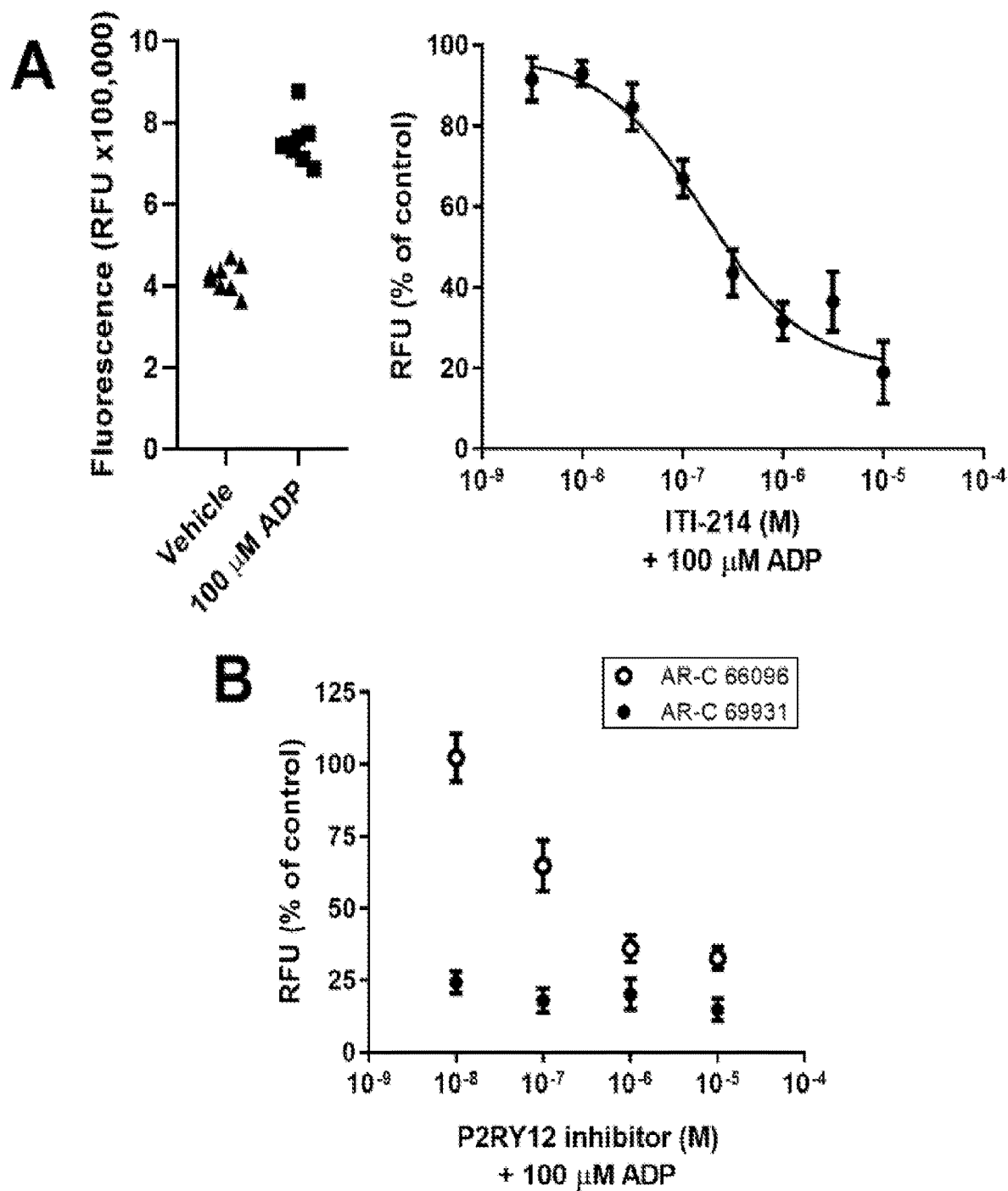
FIG. 7 generally depicts how Compound 214 inhibits ADP-induced chemotaxis in BV2 cells by enhancing cAMP and P-VASP(S157) levels.

The Applicants measure mRNA levels of four common inflammatory markers (TNF, IL1β, Ccl2, and IL6) using quantitative PCR (FIG. 7). In adult mice treated with 500 μg/kg LPS s.c. for 2 hours, mRNA expression levels of all four markers increases significantly as measured in isolated tissue samples from the striatum (FIG. 7). A dose of 10 mg/kg (Compound 214) which is delivered i.p. attenuates the following constraints: top >80% and bottom <20%. It was found that inhibition of PDE1 with ITI-214 did indeed inhibit ADP induced chemotaxis of BV2 cells in a Boyden chamber system, in which cells migrate from an upper chamber into a lower chamber containing the chemoattractant ADP. As shown in the left panel of FIG. 7A, raw fluorescence counts (relative fluorescence units or RFU), representing the cell count in the lower chamber, were used to calculate control conditions. The Vehicle condition represents the minimum migration, in which there was no ADP present. The maximum migration was shown as the 100 μM ADP condition. As shown in the right panel of FIG. 7A, compound 214 reduced chemotaxis of BV2 cells toward 100 μM ADP in a dose-dependent manner.

To confirm that the ADP induced migration in our system was mediated by P2Y12 receptors, the dose dependent inhibition of migration was additionally demonstrated with two P2Y12 inhibitors, shown in FIG. 7B. The P2Y12 inhibitors used were AR-C 66096 (open circles; documented IC50 of 6.9 nM) and AR-C 69931 (solid circles, documented IC50 of 0.4 nM), which inhibited ADP induced migration in the Boyden chamber system. The measured potency correlates with documented IC50 values. These results indicate an important role for the P2Y12 receptor in the migration response.

Figure 8:
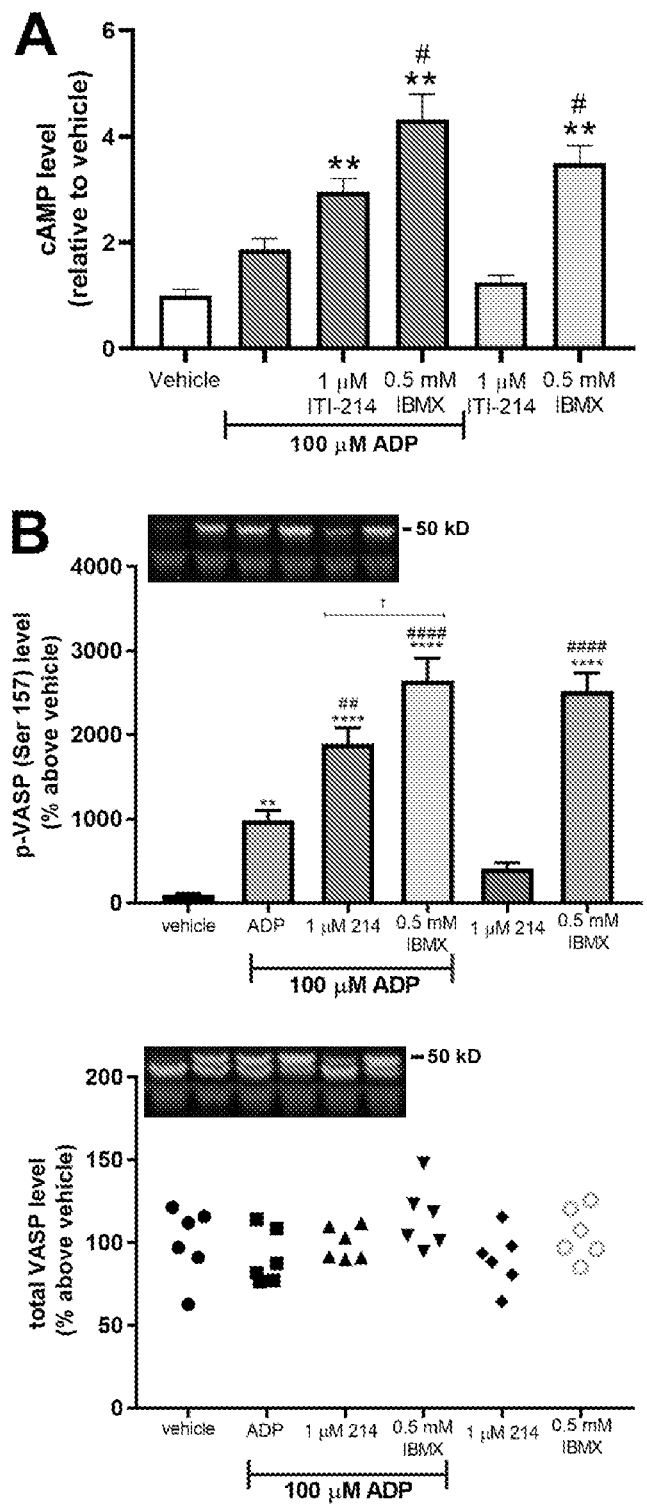
FIG. 8 illustrates the chemotaxis effect in BV2 cells treated with ITI-214 or IBMX for 30 min prior to stimulation with ADP for 5 minutes; the resulting phosphorylated VASP at S157, and the intensity of the resulting bands measured; and the total VASP levels of the tested samples.
Figure 9:
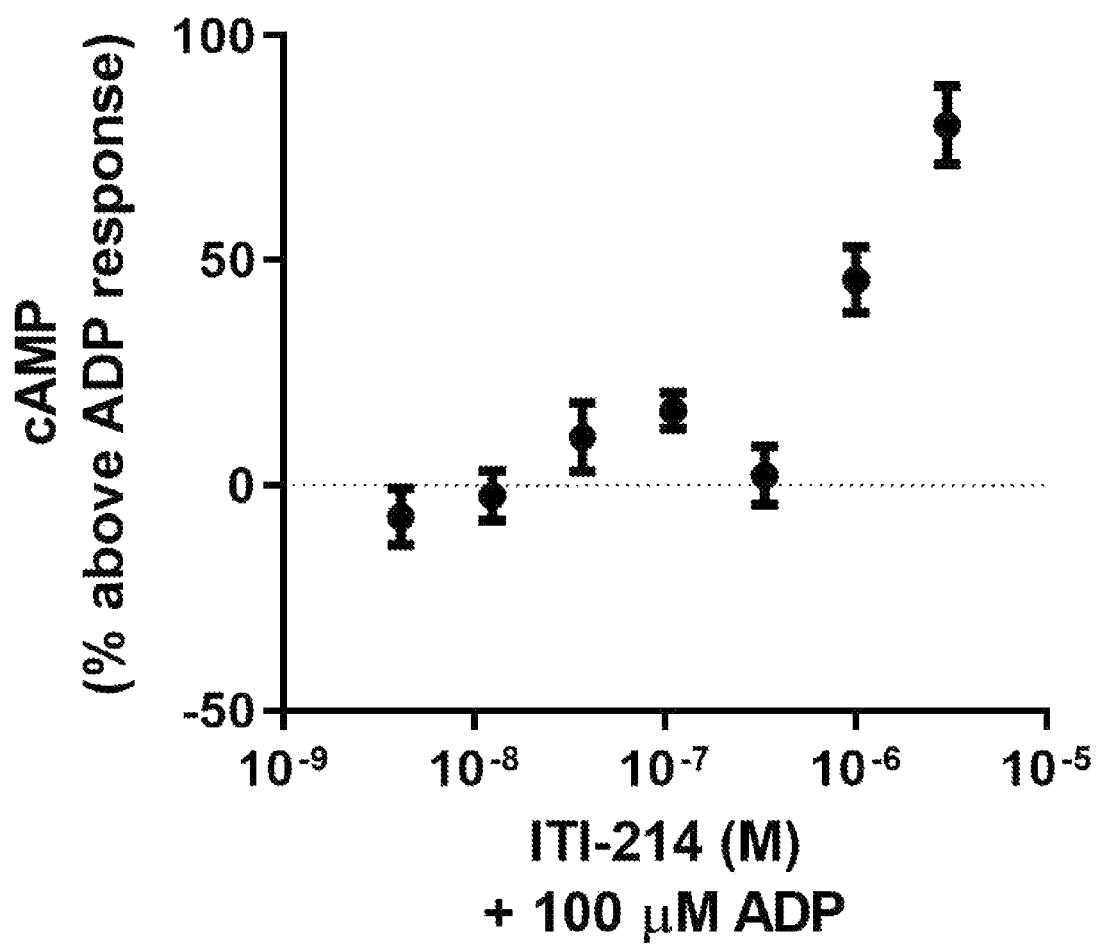
FIG. 9 illustrates the dose dependent nature of the resulting increase in cAMP following exposure to Compound 214.

In a further experiment, BV2 cells were treated with Compound 214 or IBMX for 30 min prior to stimulation with ADP for 5 minutes. cAMP levels were normalized to number of cells. Cell lysates on a Western were blotted with an antibody to phosphorylated VASP at S157, and the intensity of the resulting bands were measured (as raw signal). PDE1 inhibition with Compound 214 in BV2 cells significantly augmented ADP-induced elevations in cAMP, as measured by ELISA, and P-VASP at serine 157, as measured by Western blot (FIG. 8). There was no effect of PDE1 inhibition at baseline, consistent with the hypothesis that PDE1 is important under conditions of stimulation. The pan-PDE inhibitor, IBMX, did elevate cAMP and P-VASP levels under baseline conditions suggesting that other PDE families are important for maintaining homeostasis. Compound 214 prevents ADP-induced chemotaxis of BV2 cells by enhancing cAMP levels and phosphorylation of VASP. As with cAMP, PDE1 activity (sensitive to ITI-214) appears to contribute about 50% to the total PDE activity (sensitive to IBMX) under conditions of stimulation while having no contribution at baseline. The dose dependent nature of the increase in cAMP is illustrated in FIG. 9.

Figure 10:
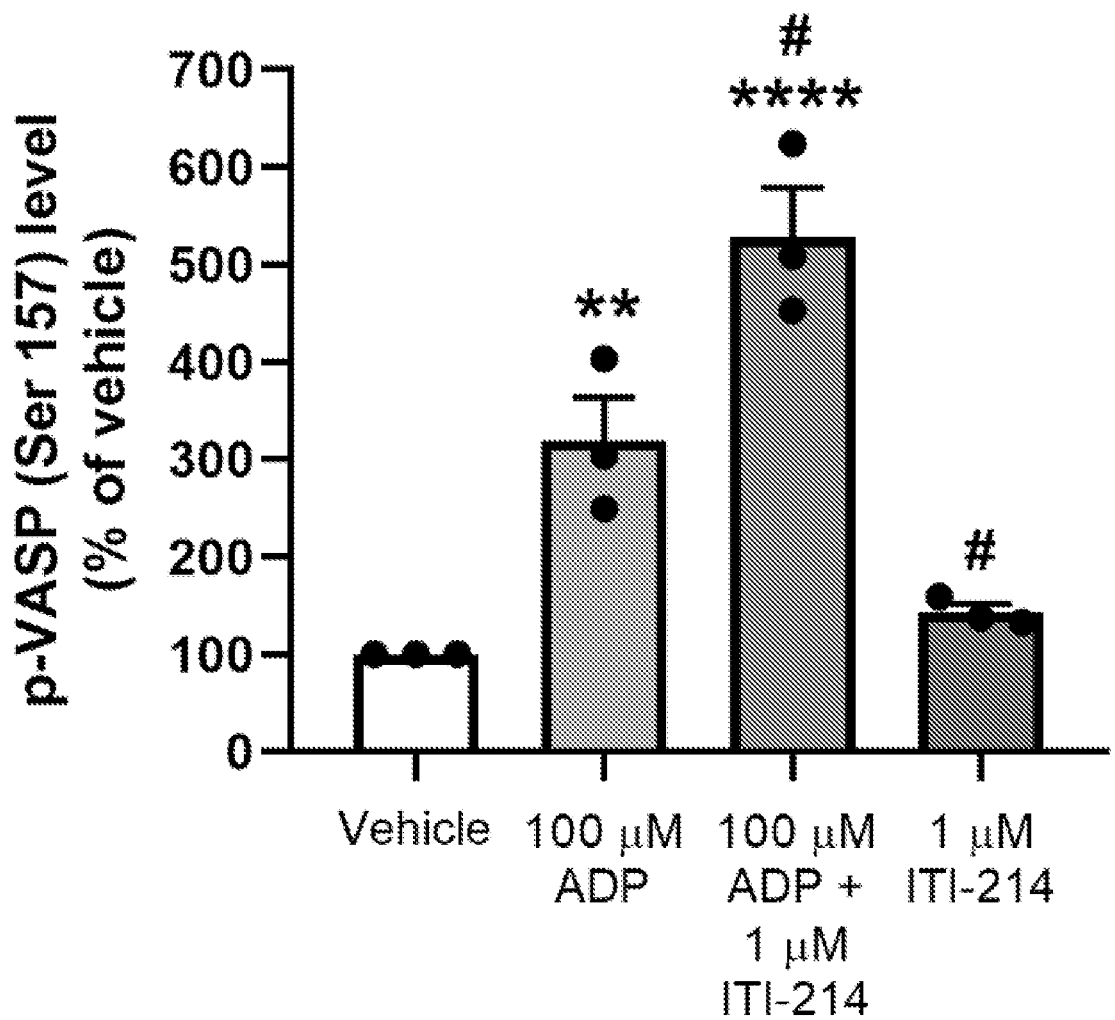
FIG. 10 illustrates the ADP-induced p-VASP (S157) levels in cultured primary rat microglia after treatment with Compound 214.

The above results were replicated in primary cultured microglia isolated from P2 rat whole brain (FIG. 10). Microglia were grown in culture for 12 days in serum-free media containing TGFb2, IL34, and cholesterol. The cells maintained properties in culture consistent with quiescent microglial-like cells, staining positive for Iba1 and maintaining a branched morphology. As with BV2 cells, addition of 1 µM ITI-214 significantly enhanced the increase in VASP phosphorylation detected after treatment with 100 µM ADP for 5 mins, while having little effect under basal conditions (FIG. 10). Replication of these data in microglia cells suggests that findings in the BV2 cells may be representative of microglial cellular responses.

Figure 11:
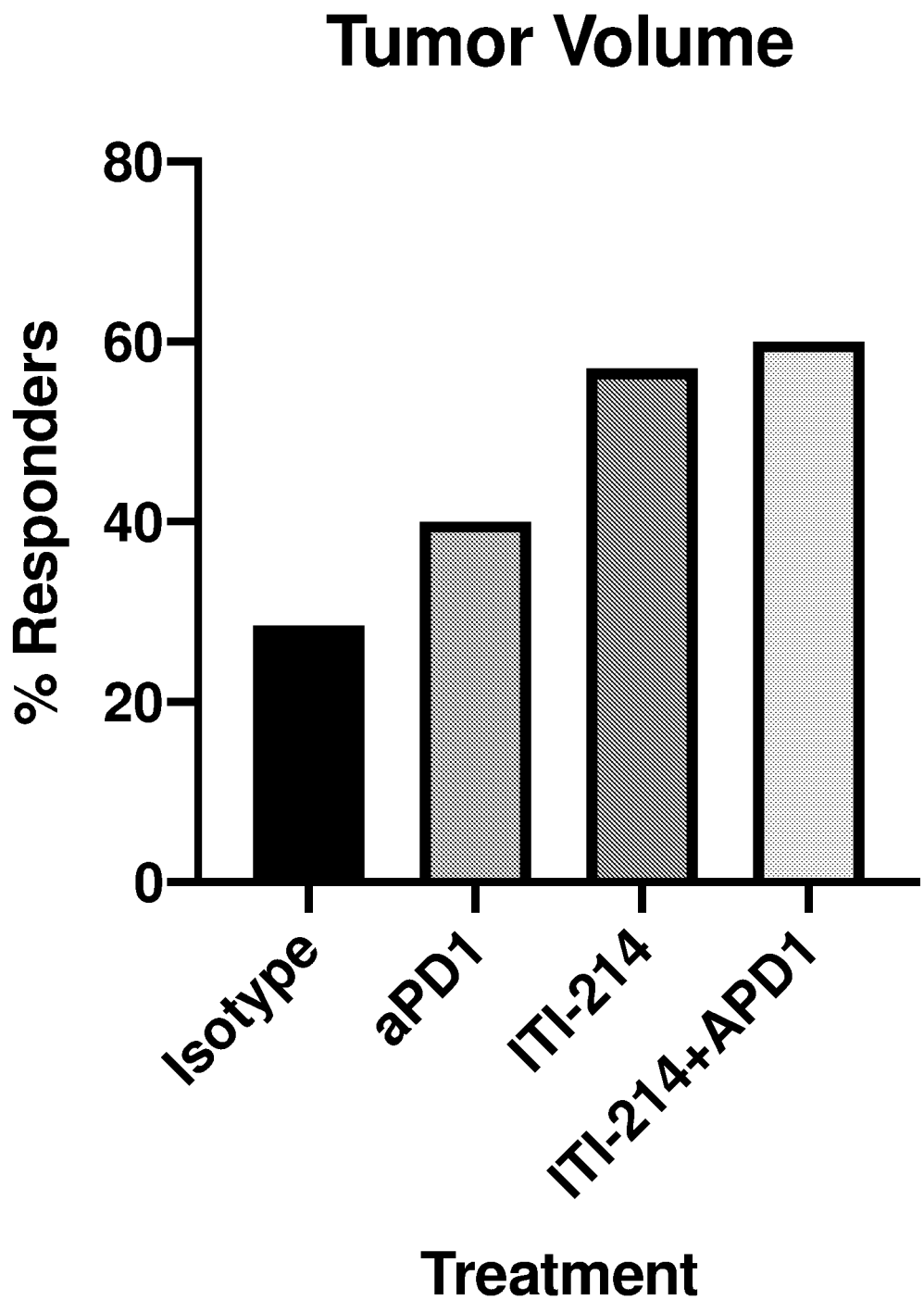
FIG. 11 illustrates the effect administration of Anti-PD-1 and Compound 214, both alone and in combination, had on tumor size in mice injected with CT26 colorectal cancer cells.

Example 9—Effect of PDE1 Treatment Alone and in Combination with Anti-PD-1 Treatment on Murine Colorectal Carcinoma Cells Tests were carried out to test the effect administration of Compound 214 had on tumor size when administered alone or in combination with a sub-threshold dose of a checkpoint inhibitor. Mice were engrafted subcutaneously with CT26 colorectal carcinoma cells. Control mice were administered 150 µg IgG (Isotype). The remaining mice were administered 1 mg Compound 214 at a frequency of 5 days a week starting at day 7; or 150 µg Anti-PD-1 (RMP1-14 monoclonal antibody, in a pH 3.5 PBS carrier), on days 7, 11, 14, 17; or both Compound 214 and Anti-PD-1. Effects on terminal tumor volume is shown in FIG. 11. Compound 214, administered both alone and in combination with the Anti-PD-1 antibody, was shown to increase the percentage of responders (i.e., those having a tumor volume <500 mm3).

Figure 12:
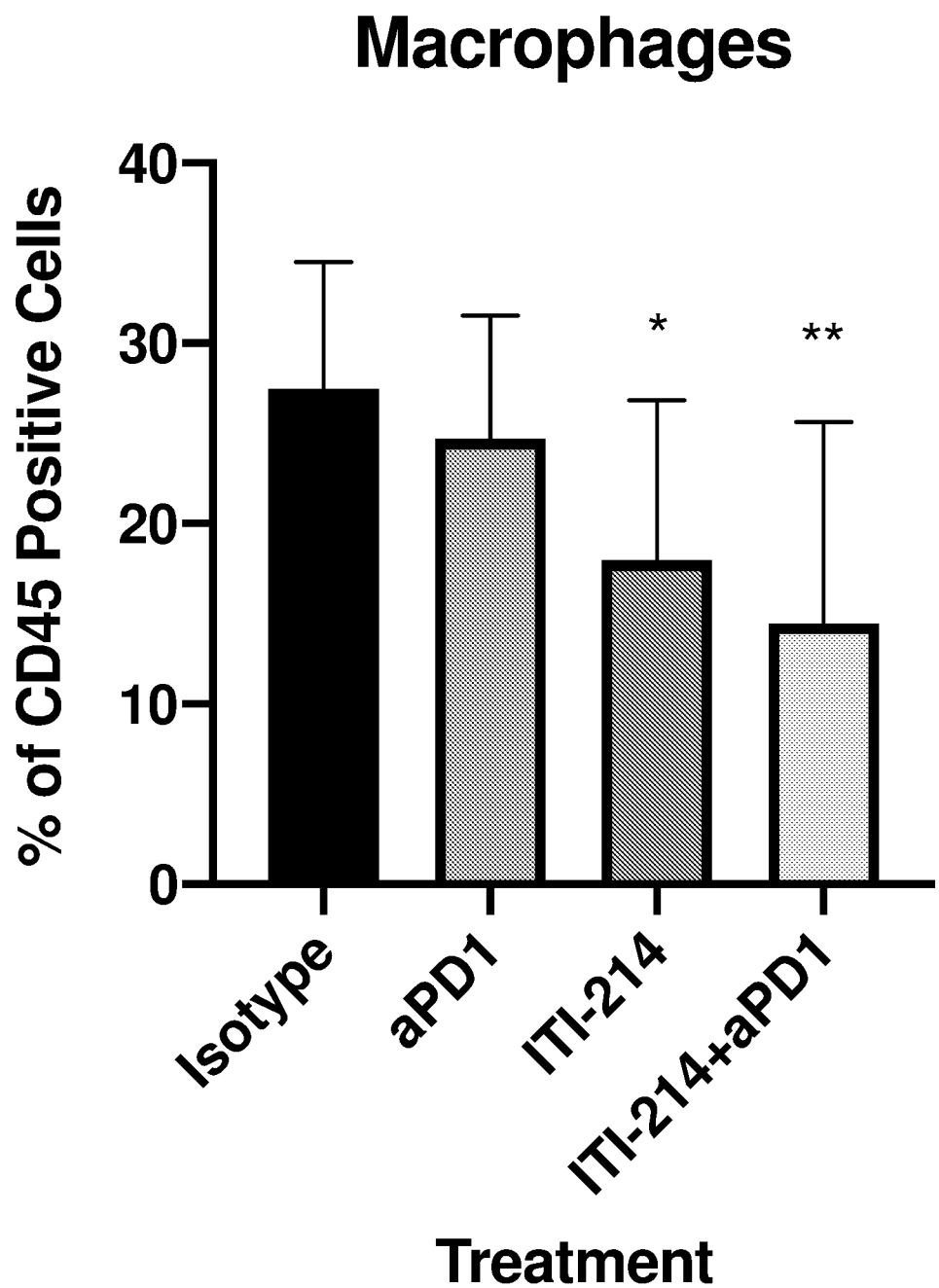
FIG. 12 illustrates the effect administration of Anti-PD-1 and Compound 214, both alone and in combination, had on CD45 positive macrophage invasion in mice injected with CT26 colorectal cancer cells.

Analysis of the affected tissue showed that Compound 214 when administered alone or in combination with an anti-PD1 antibody at a concentration of 50 mg/kg, i.p., once daily also significantly reduced the number of macrophages (CD45 positive) in the tumor microenvironment as shown in FIG. 12. Overall, Compound 214 is shown to have durable effects in the tumor microenvironment yielding a reduction in tumor volume, and consistent with a reduction in macrophage invasion.

What is claimed is:

1. A method of treating a cancer or tumor by inhibiting one or more of
   (A) cancer or tumor recruitment of immune cells;
   (B) tumor or cancer metastasis;
   (C) tumor or cancer angiogenesis;
   (D) disruption of immune surveillance;
   comprising administering a pharmaceutically effective amount of a PDE1 inhibitor, optionally in combination or association with a checkpoint inhibitor or an immunotherapy, to a subject in need thereof, wherein the PDE1 inhibitor is a compound of Formula Ia

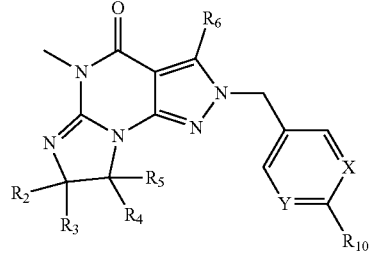

Formula Ia wherein
   (i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;
   (ii) $R_6$ is (optionally halo-substituted) phenylamino, (optionally halo-substituted) benzylamino, $C_{1-4}$alkyl, or $C_{1-4}$alkyl sulfide;
   (iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and
X and Y are independently C or N,
in free, pharmaceutically acceptable salt or prodrug form, including its enantiomers, diastereoisomers and racemates.

2. The method according to claim 1, wherein the condition is a tumor.

3. The method according to claim 1, wherein the tumor is selected from one or more of acoustic neuroma, astrocytoma, chordoma, lymphoma, craniopharyngioma, gliomas, subependymoma, medulloblastoma, meningioma, metastatic brain tumors, oligodendroglioma, pituitary tumors, primitive neuroectodermal (PNET), schwannoma, adenomas, fibroids, fibromas, hemangiomas, lipomas, myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningioma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia, leukoplakia, hemangioma, lymphangioma, carcinoma, sarcoma, blastoma, germ cell tumor, mesothelioma, malignant skin adnexal tumors, hypernephroma, seminoma, glioma, malignant meningioma, malignant schwannoma, malignant pheochromocytoma, malignant paraganglioma, melanoma, mercell cell neoplasm, cystosarcoma phylloides, or Wilms tumor.

4. The method according to claim 1, comprising administering a checkpoint inhibitor, wherein the checkpoint inhibitor is selected from one or more of inhibitors of CTLA-4, PD-1 and/or PD-L1.

5. The method according to claim 1, comprising administering a checkpoint inhibitor, wherein the checkpoint inhibitor comprises one or more members selected from nivolumab, pembrolizumab, cemiplimab, ipilimumab, avelumab, durvalumab, atezolizumab, and spartalizumab.

6. The method according to claim 1, wherein the subject is suffering from a systemic inflammatory response, a gastrointestinal inflammation-related disorder, an endocrine inflammation-related disorder, a dermatologic inflammation-related disorder, an ophthalmologic inflammation-related disorder, a neurologic inflammation-related disorder, a hematologic inflammation-related disorder, a genitourinary inflammation-related disorder, a respiratory inflammation-related disorder, a musculoskeletal inflammation-related disorder, a cardiac inflammation-related disorder, or a defined systemic inflammation-related disorder.

7. A method of mitigation of a disease, disorder or adverse effect consequent to administration of a checkpoint inhibitor therapy, the method comprising administering a pharmaceutically acceptable amount of a PDE1 inhibitor to a subject in need thereof, wherein the PDE1 inhibitor is a compound of Formula Ia

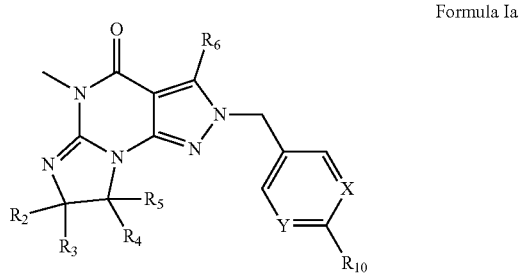

Formula Ia wherein
(i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;
(ii) $R_6$ is (optionally halo-substituted) phenylamino, (optionally halo-substituted) benzylamino, $C_{1-4}$alkyl, or $C_{1-4}$alkyl sulfide;
(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and
X and Y are independently C or N,
in free, pharmaceutically acceptable salt or prodrug form, including its enantiomers, diastereoisomers and racemates.

8. The method according to claim 7, wherein the checkpoint inhibitor therapy is administered for the treatment of a cancer or tumor.

9. The method according to claim 7, wherein the checkpoint inhibitor is an inhibitor of CTLA-4, PD-1 and/or PD-L1.

10. The method according to claim 7, wherein the disease, disorder or adverse effect consequent to administration of a checkpoint inhibitor therapy is a systemic inflammatory response, a gastrointestinal inflammation-related disorder, an endocrine inflammation-related disorder, a dermatologic inflammation-related disorder, an ophthalmologic inflammation-related disorder, a neurologic inflammation-related disorder, a hematologic inflammation-related disorder, a genitourinary inflammation-related disorder, a respiratory inflammation-related disorder, a musculoskeletal inflammation-related disorder, a cardiac inflammation-related disorder, or a defined systemic inflammation-related disorder.

11. A method of suppressing macrophage or microglial recruitment to metastatic cells comprising administering a pharmaceutically acceptable amount of a PDE1 inhibitor to a subject in need thereof, wherein the PDE1 inhibitor is a compound of Formula Ia

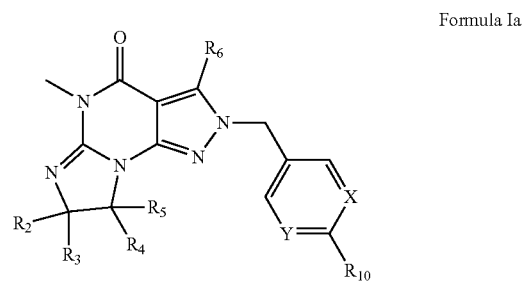

Formula Ia wherein
(i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;
(ii) $R_6$ is (optionally halo-substituted) phenylamino, (optionally halo-substituted) benzylamino, $C_{1-4}$alkyl, or $C_{1-4}$alkyl sulfide;
(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and
X and Y are independently C or N,
in free, pharmaceutically acceptable salt or prodrug form, including its enantiomers, diastereoisomers and racemates.

12. The method according to claim 11, wherein the macrophage or microglial recruitment to metastatic cells is mediated at least in part by CCL2.

13. The method according to claim 11, wherein the PDE1 inhibitor is administered in combination with a checkpoint inhibitor, e.g., wherein the checkpoint inhibitor is an inhibitor of CTLA-4, PD-1 and/or PD-L1.

14. The method according to claim 1, wherein the PDE1 inhibitor is selected from any of the following

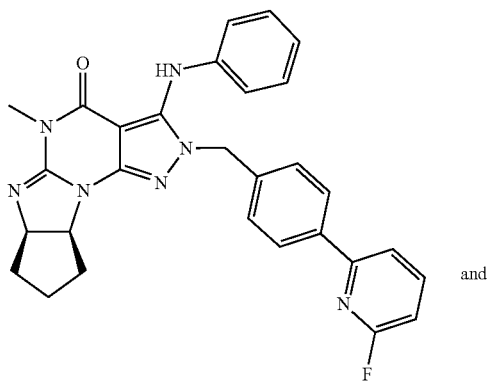

and

-continued

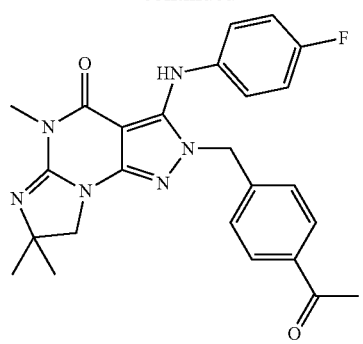

in free or pharmaceutically acceptable salt form.

15. The method according to claim 1, wherein the PDE1 inhibitor is

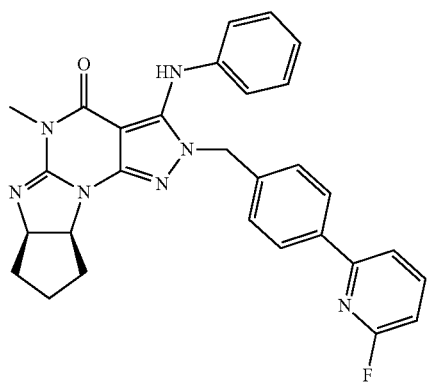 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

16. The method according to claim 1, wherein the PDE1 inhibitor is

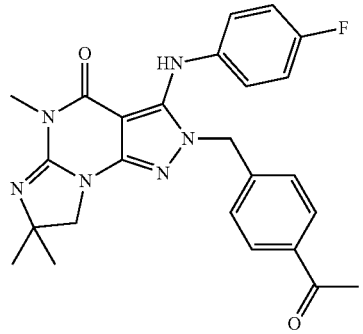

in free or pharmaceutically acceptable salt form.

17. The method according to claim 7, wherein the PDE1 inhibitor is selected from any of the following

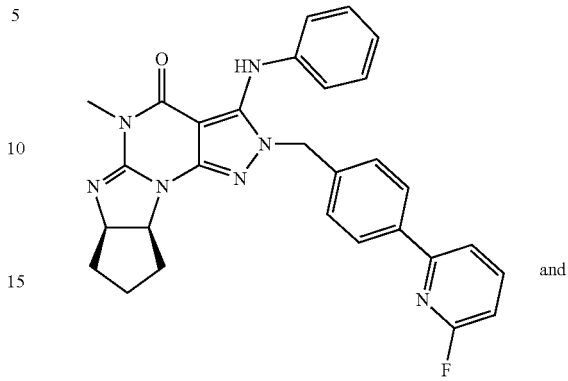

and

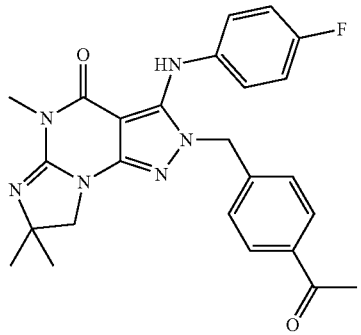 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

18. The method according to claim 7, wherein the PDE1 inhibitor is

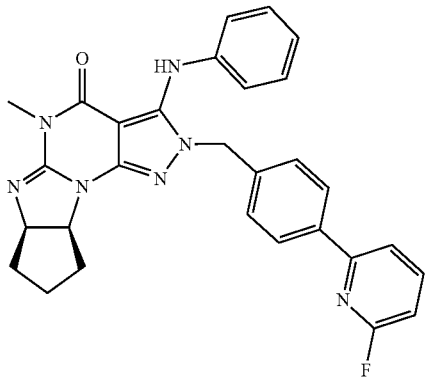 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

19. The method according to claim 7, wherein the PDE1 inhibitor is

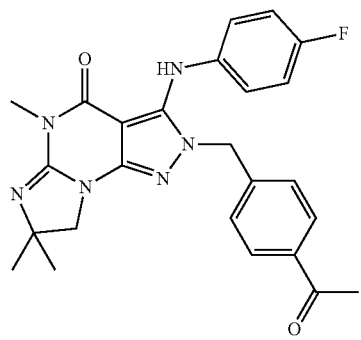

in free or pharmaceutically acceptable salt form.

20. The method according to claim 11, wherein the PDE1 inhibitor is selected from any of the following

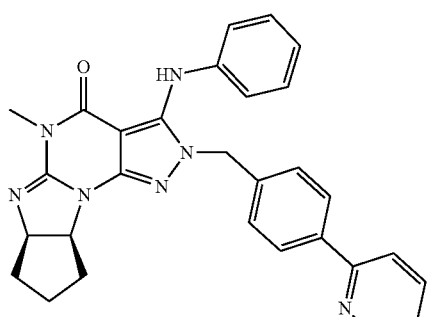

and

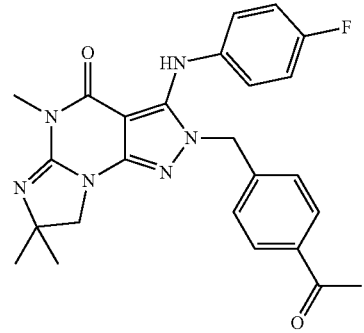 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

21. The method according to claim 11, wherein the PDE1 inhibitor is

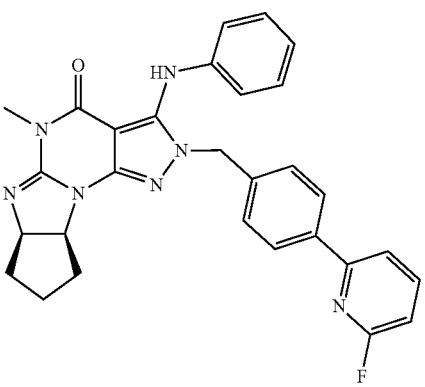 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

22. The method according to claim 11, wherein the PDE1 inhibitor is

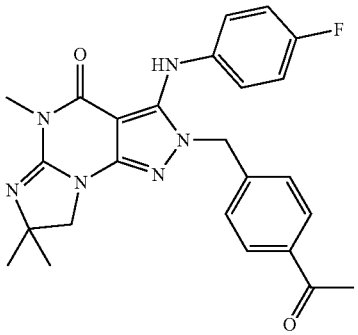 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

* * * * *